US006906176B2

(12) United States Patent
Ley et al.

(10) Patent No.: US 6,906,176 B2
(45) Date of Patent: Jun. 14, 2005

(54) ENTEROKINASE CLEAVAGE SEQUENCES

(75) Inventors: Arthur Charles Ley, Newton, MA (US); Christopher Jon Luneau, Salem, MA (US); Robert Charles Ladner, Ijamsville, MD (US)

(73) Assignee: Dyax Corp., Cambridge, MA (US)

( * ) Notice: Subject to any disclaimer, the term of this patent is extended or adjusted under 35 U.S.C. 154(b) by 1 day.

(21) Appl. No.: 09/884,767

(22) Filed: Jun. 19, 2001

(65) Prior Publication Data

US 2002/0192789 A1 Dec. 19, 2002

Related U.S. Application Data

(60) Provisional application No. 60/367,345, filed on Jun. 19, 2000.

(51) Int. Cl.$^7$ ............................ C07K 14/00; C12N 9/50
(52) U.S. Cl. ....................................... 530/350; 435/219
(58) Field of Search ........................... 435/219; 530/350

(56) References Cited

U.S. PATENT DOCUMENTS

| 5,223,409 A | 6/1993 | Ladner et al. ............. 435/69.7 |
| 5,403,484 A | 4/1995 | Ladner et al. ............ 435/235.1 |
| 5,432,018 A | 7/1995 | Dower et al. ................... 435/5 |
| 5,571,698 A | 11/1996 | Ladner et al. .................. 435/6 |
| 5,665,566 A | 9/1997 | LaVallie .................... 435/69.3 |

FOREIGN PATENT DOCUMENTS

| GB | 2 241 703 | 9/1991 |
| WO | WO 92/15679 | 9/1992 |
| WO | WO 93/03157 | 2/1993 |
| WO | WO 01/79481 | 10/2001 |

OTHER PUBLICATIONS

Denhez, F., et al. (1994) J. Biol. Chem.. 269(23), 16170–17179.*
Escriva, H., et al. (1997) Proc. Natl. Acad. Sci., USA 94, 6803–6808.*
Dear, T.N., et al. (1993) Proc. Natl. Acad. Sci, USA 90, 4431–4435.*
Hollander, M.C., et al. Nucl. Acids Res. 24(9), 1589–1593.*
Kerfeld, C.A., et al. (1994) Biochemistry 33, 2178–2184.*
Morris, C.J., et al. (1995) J. Biol. Chem. 177(23), 6825–6831.*
International Search Report, mailed Dec. 5, 2002, PCT/US01/19539.
Antonowicz, I., Ciba Found. Symp., 70: 169–187 (1979).
Atkinson and Smith, Oligonucleotide Synthesis, M. J. Gain, ed. p. 35–82 (1984).

Collins–Racie et al., Biotechnology, 13(9): 982–987 (1995).
Hopp et al., BioTechnology, 6: 1204–1210 (1988).
Houghten, R.A., Proc. Natl. Acad. Sci. USA, 82(15): 5131–5135 (1985).
Kay et al., Phage Display of Peptides and Proteins: A Laboratory Manual, Academic Press, Inc.,San Diego (1996); contents only.
Kelley et al., Genetic Engineering Principles and Methods, (Setlow, J.K., ed.), Plenum Press, NY., (1990) vol. 12, pp. 1–19.
Kitamoto et al., Proc. Natl. Acad. Sci. USA, 91(16): 7588–7592 (1994).
LaVallie et al., J. Biol. Chem., 268(31): 23311–23317 (1993).
Liepnieks et al., J. Biol. Chem., 254(5): 1677–1683 (1979).
Light et al., Anal. Biochem., 106: 199–206 (1980).
Light and Janska, Trends Biochem. Sci., 14(3) 110–112 (1989).
Lu et al., J. Biol. Chem., 272(50): 31293–31300 (1997).
Lutz–Freyermuth et al., Proc. Natl. Acad. Sci. USA, 87: 6393–6397 (1990).
Martin et al., Cell, 63: 843–849 (1990).
Martin et al., Science, 255:192–194 (1992).
McBride and Caruthers, Tetrahedron Letters 22: 245 (1983).
Merrifield, J. Am. Chem. Soc., 85: 2149 (1963).
Munro & Pelham, Cell, 46: 291–300 (1986).
Myers et al., Nucl. Acids Res., 13: 3131–3145 (1985).
Myers et al., Science, 229: 242–246 (1985).
Ojala, et al., Biochem. Biophys. Res. Commun. 284(3): 777–784 (2001).
Oliphant et al., Gene, 44: 177–183, (1986).
Sambrook et al., Molecular Cloning, A Laboratory Manual, $2^{nd}$ ed., Cold Spring Harbor Laboratory Press, Cold Spring Harbor, N.Y. (1989); contents only.
Skinner et al., J. Biol. Chem., 266: 14163–14166 (1991).
Steward et al., Solid Phase Peptide Synthesis, W.H. Freeman Co., San Francisco (1989); contents only.
Vozza et al., Biotechnology (NY), 14(1): 77–81 (1996).
Wang et al., Biol. Chem. Hoppe Seyler, 376(11): 681–684 (1995).
Ward et al., Nature, 341: 544–546 (1989).

* cited by examiner

Primary Examiner—Charles L. Patterson, Jr.
(74) Attorney, Agent, or Firm—Fish & Richardson P.C.

(57) ABSTRACT

Novel enterokinase cleavage sequences are provided. Also disclosed are methods for the rapid isolation of a protein of interest present in a fusion protein construct including a novel enterokinase cleavage sequence of the present invention and a ligand recognition sequence for capturing the fusion construct on a solid substrate. Preferred embodiments of the present invention show rates of cleavage up to thirty times that of the known enterokinase cleavage substrate $(Asp)_4$-Lys-Ile.

27 Claims, 2 Drawing Sheets

SEQUENCE LISTING

<160> NUMBER OF SEQ ID NOS: 217

<210> SEQ ID NO 1
<211> LENGTH: 7
<212> TYPE: PRT

```
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (1)..(1)
<223> OTHER INFORMATION: Xaa1 is an optional amino acid which, if
      present, is Ala, Asp, Glu, Phe, Gly, Ile, Asn, Ser, or Val
<221> NAME/KEY: MISC_FEATURE
<222> LOCATION: (2)..(2)
<223> OTHER INFORMATION: Xaa2 is an optional amino acid which, if
      present, is Ala, Asp, Glu, His, Ile, Leu, Met, Gln or Ser
<221> NAME/KEY: MISC_FEATURE
<222> LOCATION: (3)..(3)
<223> OTHER INFORMATION: Xaa3 is an optional amino acid which, if
      present, is Asp, Glu, Phe, His, Ile, Met, Asn, Pro, Val, or Trp
<221> NAME/KEY: MISC_FEATURE
<222> LOCATION: (4)..(4)
<223> OTHER INFORMATION: Xaa4 is Ala, Asp, Glu, or Thr
<221> NAME/KEY: MISC_FEATURE
<222> LOCATION: (7)..(7)
<223> OTHER INFORMATION: Xaa7 is any amino acid

<400> SEQUENCE: 1

Xaa Xaa Xaa Xaa Asp Arg Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (1)..(1)
<223> OTHER INFORMATION: Xaa1 is an optional amino acid which, if
      present, is Asp or Glu
<221> NAME/KEY: MISC_FEATURE
<222> LOCATION: (2)..(2)
<223> OTHER INFORMATION: Xaa2 is an optional amino acid which, if
      present, is Val
<221> NAME/KEY: MISC_FEATURE
<222> LOCATION: (3)..(3)
<223> OTHER INFORMATION: Xaa3 is an optional amino acid which, if
      present, is Tyr
<221> NAME/KEY: MISC_FEATURE
<222> LOCATION: (4)..(4)
<223> OTHER INFORMATION: Xaa4 is Asp, Glu or Ser
<221> NAME/KEY: MISC_FEATURE
<222> LOCATION: (7)..(7)
<223> OTHER INFORMATION: Xaa7 is any amino acid

<400> SEQUENCE: 2

Xaa Xaa Xaa Xaa Glu Arg Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (7)..(7)
<223> OTHER INFORMATION: Xaa is any amino acid

<400> SEQUENCE: 3

Asp Ile Asn Asp Asp Arg Xaa
1               5

<210> SEQ ID NO 4
<211> LENGTH: 7
<212> TYPE: PRT
<213> ORGANISM: Artificial Sequence
```

```
-continued

<220> FEATURE:
<223> OTHER INFORMATION: synthetic enterokinase cleavage sequence
<221> NAME/KEY: MISC_FEATURE
<222> LOCATION: (7)..(7)
<223> OTHER INFORMATION: Xaa is any amino acid

<400> SEQUENCE: 4

Gly Asn Tyr Thr Asp Arg Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: streptavidin binding sequence

<400> SEQUENCE: 5

Cys His Pro Gln Phe Cys
1               5

<210> SEQ ID NO 6
<211> LENGTH: 4
<212> TYPE: PRT
<213> ORGANISM: Artificial Sequence
<220> FEATURE:
<223> OTHER INFORMATION: streptavidin binding sequence

<400> SEQUENCE: 6

His Pro Gln Phe
1

<210> SEQ ID NO 7
<211> LENGTH: 9
<212> TYPE: PRT
<213> ORGANISM: Artificial Sequence
<220> FEATURE:
<223> OTHER INFORMATION: streptavidin binding sequence

<400> SEQUENCE: 7

Cys His Pro Gln Phe Cys Ser Trp Arg
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (6)..(6)
<223> OTHER INFORMATION: Xaa is Ile (natural trypsinogen site) or any
      amino acid (synthetic cleavage sites)

<400> SEQUENCE: 8

Asp Asp Asp Asp Lys Xaa
1               5

<210> SEQ ID NO 9
<211> LENGTH: 86
<212> TYPE: PRT
<213> ORGANISM: Artificial Sequence
<220> FEATURE:
<223> OTHER INFORMATION: exogenous display polypeptide of a phage
      display library
<221> NAME/KEY: MISC_FEATURE
<222> LOCATION: (43)..(55)
<223> OTHER INFORMATION: X is any amino acid except Cys
```

-continued

```
<400> SEQUENCE: 9

Ala Glu Trp His Pro Gln Phe Ser Ser Pro Ser Ala Ser Arg Pro Ser
1               5                   10                  15

Glu Gly Pro Cys His Pro Gln Phe Pro Arg Cys Tyr Ile Glu Asn Leu
            20                  25                  30

Asp Glu Phe Arg Pro Gly Gly Ser Gly Gly Xaa Xaa Xaa Xaa Xaa
        35                  40                  45

Xaa Xaa Xaa Xaa Xaa Xaa Gly Ala Gln Ser Asp Gly Gly Ser
    50                  55                  60

Thr Glu His Ala Glu Gly Gly Ser Ala Asp Pro Ser Tyr Ile Glu Gly
65                  70                  75                  80

Arg Ile Val Gly Ser Ala
                85

<210> SEQ ID NO 10
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 10

Tyr Glu Trp Gln Asp Arg Thr
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 11

Asn Ser Ile Lys Asp Arg Val
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 12

Ala Lys Ala Thr Glu Arg His
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 13

Leu Gly Lys Val Asp Arg Thr
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic enterokinase cleavage sequence
```

```
<400> SEQUENCE: 14

Gly Gly Met Ala Asp Lys Phe
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 15

Gly His Trp Leu Asp Lys Asn
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 16

Asn Lys Ala Lys Asp Arg Met
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 17

Ser Glu Asn Phe Asp Lys Asn
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 18

Leu Asp Trp Glu Asp Arg Ala
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 19

Ser Thr Asp Ala Glu Arg Met
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic enterokinase cleavage sequence
```

-continued

```
<400> SEQUENCE: 20

His Thr Phe Ser Asp Arg Gln
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 21

Gly Ser Gly Gly Asp Arg Leu
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 22

Gly Phe Tyr Asn Asp Arg Met
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 23

Ile Met Pro Gln Asp Lys Ser
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 24

Gly Gly Val Glu Asp Arg Ser
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 25

Trp Gln Glu Ser Asp Arg Ala
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 26
```

```
Gly Ser Gly Gly Asp Arg His
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 27

Gly His Ile Phe Asp Arg Ser
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 28

Gly Ser Gly Gly Glu Lys Leu
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 29

Ser Gly Gly Glu Asp Arg Met
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 30

Gly Ser Gly Gly Glu Arg Thr
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 31

Pro Asp Pro Gln Glu Arg Gln
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 32
```

```
Tyr Ile Met Gly Asp Arg Thr
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 33

Gln Asn His Ser Asp Arg Thr
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 34

Ile Ala His Gly Glu Arg Ala
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 35

His Glu Met Asn Asp Arg His
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 36

Thr His Asn Gly Glu Lys Met
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 37

His Asp Glu Ala Glu Lys Thr
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 38

Gly Tyr Trp Ile Asp Arg Ser
```

```
<210> SEQ ID NO 39
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 39

Gly Ser Gly Gly Glu Arg Leu
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 40

Ser Gly Gly Ser Asp Arg Leu
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 41

Ala Gln Tyr Met Asp Leu Met
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 42

Gly Ser Gly Gly Glu Arg Asn
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 43

Gly Ser Gly Gly Glu Asn Gly
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 44

Glu Asn Tyr Glu Glu Arg Thr
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 45

Asn Ile Tyr Gly Asp Arg Ile
1               5

<210> SEQ ID NO 46
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 46

Gly Gly Phe Val Asp Lys Gln
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 47

Gly Ser Gly Gly Glu Lys Val
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 48

Gly Lys Phe Glu Asp Arg Asn
1               5

<210> SEQ ID NO 49
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 49

Pro Ala His Thr Asp Arg Asp
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 50

Gln Gln Met His Asp Arg Phe
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 51

Asp Met Gly Tyr Asp Arg Gly
1               5

<210> SEQ ID NO 52
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 52

Ser Gly Gly Asp Glu Lys Glu
1               5

<210> SEQ ID NO 53
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 53

Ile Glu Ser Ala Asp Arg Thr
1               5

<210> SEQ ID NO 54
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 54

Arg Asn Met Asp Glu Arg Ala
1               5

<210> SEQ ID NO 55
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 55

Thr Val Gly Met Asp Lys Phe
1               5

<210> SEQ ID NO 56
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 56

Gly Ser Gly Gly Asp Arg Phe
1               5
```

```
<210> SEQ ID NO 57
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 57

Arg His Asn Tyr Asp Arg Ile
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 58

Val Tyr His Val Asp Lys Met
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 59

Gly Ser Gly Gly Glu Arg Asn
1               5

<210> SEQ ID NO 60
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 60

Gly Gly Lys Tyr Asp Arg Met
1               5

<210> SEQ ID NO 61
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 61

Gly Gly Asn Asp Asp Lys Met
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 62

Ala Ala Val Glu Asp Arg Asn
1               5

<210> SEQ ID NO 63
```

```
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 63

Pro Cys Lys Asp Glu Arg Phe
1               5

<210> SEQ ID NO 64
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 64

Gly Ser Glu Leu Asp Arg Met
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 65

Phe Ser Glu Glu Asp Arg Met
1               5

<210> SEQ ID NO 66
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 66

Gly Ser Gly Gly Glu Arg Phe
1               5

<210> SEQ ID NO 67
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 67

Tyr Gln Pro Thr Asp Arg Thr
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 68

Ser Gly Gly Glu Asp Arg Met
1               5

<210> SEQ ID NO 69
<211> LENGTH: 7
```

```
<212> TYPE: PRT
<213> ORGANISM: Artificial Sequence
<220> FEATURE:
<223> OTHER INFORMATION: synthetic enterokinase cleavage sequence

<400> SEQUENCE: 69

Thr Glu Gln Met Asp Arg Met
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 70

Gln Pro Phe Asp Asp Arg Asp
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 71

Gly Ser Gly Gly Glu Arg Thr
1               5

<210> SEQ ID NO 72
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 72

Glu Gly Met Thr Asp Arg Leu
1               5

<210> SEQ ID NO 73
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 73

Glu Ile Pro Glu Asp Arg Met
1               5

<210> SEQ ID NO 74
<211> LENGTH: 7
<212> TYPE: PRT
<213> ORGANISM: Artificial Sequence
<220> FEATURE:
<223> OTHER INFORMATION: natural enterokinase cleavage sequence

<400> SEQUENCE: 74

Gly Asp Asp Asp Asp Lys Ile
1               5

<210> SEQ ID NO 75
<211> LENGTH: 7
<212> TYPE: PRT
```

<213> ORGANISM: Artificial Sequence
<220> FEATURE:
<223> OTHER INFORMATION: synthetic enterokinase cleavage sequence

<400> SEQUENCE: 75

Gly Ser Gly Gly Glu Arg Ser
1               5

<210> SEQ ID NO 76
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 76

His Gly Tyr Glu Glu Arg Met
1               5

<210> SEQ ID NO 77
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 77

Lys Pro Met Glu Glu Arg Met
1               5

<210> SEQ ID NO 78
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 78

Ser Gly Gly Asn Asp Arg Met
1               5

<210> SEQ ID NO 79
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 79

Gly Gly Thr Asp Asp Arg Phe
1               5

<210> SEQ ID NO 80
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 80

Asp Val Tyr Ser Glu Arg Met
1               5

<210> SEQ ID NO 81
<211> LENGTH: 7
<212> TYPE: PRT
<213> ORGANISM: Artificial Sequence

```
<220> FEATURE:
<223> OTHER INFORMATION: synthetic enterokinase cleavage sequence

<400> SEQUENCE: 81

Asp Val Tyr Ser Glu Arg Met
1               5

<210> SEQ ID NO 82
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 82

Gly Ser Gly Gly Asp Arg Asn
1               5

<210> SEQ ID NO 83
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 83

Asp Val Thr Ala Asp Asp Arg
1               5

<210> SEQ ID NO 84
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 84

Ala Glu Phe Ala Asp Arg Phe
1               5

<210> SEQ ID NO 85
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 85

Asn Asn Ser Asp Glu Lys Ile
1               5

<210> SEQ ID NO 86
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 86

Pro Gly Gly Asp Asp Arg Trp
1               5

<210> SEQ ID NO 87
<211> LENGTH: 7
<212> TYPE: PRT
<213> ORGANISM: Artificial Sequence
<220> FEATURE:
```

<223> OTHER INFORMATION: synthetic enterokinase cleavage sequence

<400> SEQUENCE: 87

Ser Gly Gly Glu Glu Arg Val
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 88

Val Trp Pro Asp Asp Arg Ser
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 89

His Arg Gln Thr Asp Arg Met
1               5

<210> SEQ ID NO 90
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 90

Lys Glu Ala Glu Asp Arg Ala
1               5

<210> SEQ ID NO 91
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 91

Val Gly Asp Asp Glu Arg His
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 92

Asn Ser Met Ala Asp Arg Asn
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic enterokinase cleavage sequence

```
<400> SEQUENCE: 93

Thr Glu Phe Glu Asp Lys Trp
1               5

<210> SEQ ID NO 94
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 94

Glu Ser Gly Gly Glu Arg Asp
1               5

<210> SEQ ID NO 95
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 95

Asn Asn Tyr Trp Asp Arg Met
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 96

Phe Ser Glu Glu Asp Arg Met
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 97

Glu Met His Glu Glu Arg Met
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 98

Asp Gln Met Glu Asp Arg Gln
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic enterokinase cleavage sequence
```

```
<400> SEQUENCE: 99

Glu Trp Lys Met Asp Arg Met
1               5

<210> SEQ ID NO 100
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 100

Ser Tyr Thr Trp Asp Arg Ser
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 101

Ser Phe Met Leu Asp Arg Met
1               5

<210> SEQ ID NO 102
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 102

Thr Glu Val Asp Asp Arg His
1               5

<210> SEQ ID NO 103
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 103

Gly Asp Gln Glu Asp Arg Met
1               5

<210> SEQ ID NO 104
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 104

His Asn Ile Asp Asp Arg Ile
1               5

<210> SEQ ID NO 105
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 105
```

-continued

```
Ala Ser Trp Glu Asp Arg Thr
1               5

<210> SEQ ID NO 106
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 106

Gly Gly Glu Asp Asp Arg Ser
1               5

<210> SEQ ID NO 107
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 107

Asp Ile Gln Asp Glu Arg Asn
1               5

<210> SEQ ID NO 108
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 108

Asp Thr His Ala Asp Lys Ser
1               5

<210> SEQ ID NO 109
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 109

Gly Ser Gly Gly Asp Arg Met
1               5

<210> SEQ ID NO 110
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 110

Gly Glu Ile Met Asp Arg Ser
1               5

<210> SEQ ID NO 111
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 111
```

```
Gly Ser Gly Gly Asp Lys Thr
1               5
```

<210> SEQ ID NO 112
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 112

```
Gly Ser Gly Gly Asp Arg Ala
1               5
```

<210> SEQ ID NO 113
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 113

```
Gly Asp His Leu Asp Arg Met
1               5
```

<210> SEQ ID NO 114
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 114

```
Gly Gln Gln Asp Asp Arg Gln
1               5
```

<210> SEQ ID NO 115
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 115

```
Ala Leu Ala Ala Asp Arg Met
1               5
```

<210> SEQ ID NO 116
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 116

```
Val Gly Phe Asp Asp Arg Thr
1               5
```

<210> SEQ ID NO 117
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 117

Tyr Ala Gln Asp Glu Arg Thr

```
<210> SEQ ID NO 118
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 118

Gly Gly Arg Glu Glu Arg Asn
1               5

<210> SEQ ID NO 119
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 119

Gly Ser Gly Gly Asp Arg Met
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 120

Gly Ser Gly Gly Asp Arg Glu
1               5

<210> SEQ ID NO 121
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 121

Ile Ala Tyr Gln Asp Arg Met
1               5

<210> SEQ ID NO 122
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 122

Ser Gly Gly Glu Asp Arg Ala
1               5

<210> SEQ ID NO 123
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 123

Leu Glu His Ser Asp Arg Val
1               5
```

```
<210> SEQ ID NO 124
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 124

Phe Lys Pro Asp Asp Arg Met
1               5

<210> SEQ ID NO 125
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 125

Val Pro Met Ala Asp Arg Ser
1               5

<210> SEQ ID NO 126
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 126

Gly Ser Gly Gly Glu Arg Ala
1               5

<210> SEQ ID NO 127
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 127

Asn Asp Asn Asp Glu Arg Ala
1               5

<210> SEQ ID NO 128
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 128

Gly Asn Tyr Thr Asp Arg Met
1               5

<210> SEQ ID NO 129
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 129

Gly Ser Gly Gly Glu Arg Val
1               5
```

```
<210> SEQ ID NO 130
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 130

Asp Glu Val His Asp Arg Thr
1               5

<210> SEQ ID NO 131
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 131

Gln His Asp Gly Asp Lys Thr
1               5

<210> SEQ ID NO 132
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 132

Thr Val Arg Ser Glu Lys Gly
1               5

<210> SEQ ID NO 133
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 133

Ser Gly Gly Thr Asp Arg Ile
1               5

<210> SEQ ID NO 134
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 134

Val Met Glu Asp Asp Arg Ala
1               5

<210> SEQ ID NO 135
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 135

Gly Ser Gly Gly Glu Arg Met
1               5
```

```
<210> SEQ ID NO 136
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 136

Ile Glu His Asp Asp Arg Met
1               5

<210> SEQ ID NO 137
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 137

Phe Ser Glu Glu Asp Arg Met
1               5

<210> SEQ ID NO 138
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 138

Phe Ser Glu Glu Asp Arg Met
1               5

<210> SEQ ID NO 139
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 139

Asp Val Tyr Ser Glu Arg Met
1               5

<210> SEQ ID NO 140
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 140

Asp Met Phe Asp Asp Arg Met
1               5

<210> SEQ ID NO 141
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 141

Phe Ser Glu Glu Asp Arg Met
1               5

<210> SEQ ID NO 142
```

<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 142

Glu His Leu Phe Asp Arg Met
1               5

<210> SEQ ID NO 143
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 143

Ser Trp Ile Ser Asp Arg Val
1               5

<210> SEQ ID NO 144
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 144

Asn Asp Glu Asp Asp Arg Met
1               5

<210> SEQ ID NO 145
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 145

Ser Leu Asp Asp Asp Arg Thr
1               5

<210> SEQ ID NO 146
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 146

Gly Ser Gly Gly Asp Arg Asp
1               5

<210> SEQ ID NO 147
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 147

Pro His Ile Glu Asp Arg Met
1               5

<210> SEQ ID NO 148
<211> LENGTH: 7

```
<212> TYPE: PRT
<213> ORGANISM: Artificial Sequence
<220> FEATURE:
<223> OTHER INFORMATION: synthetic enterokinase cleavage sequence

<400> SEQUENCE: 148

Ser Gly Gly Asp Asp Arg His
1               5

<210> SEQ ID NO 149
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 149

Glu Val Phe Ala Asp Arg Ser
1               5

<210> SEQ ID NO 150
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 150

Gly Leu Ala Glu Asp Arg Thr
1               5

<210> SEQ ID NO 151
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 151

Ser Gly Gly Asp Asp Arg Leu
1               5

<210> SEQ ID NO 152
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 152

Ser Gly Gly Asp Asp Arg Met
1               5

<210> SEQ ID NO 153
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 153

Gly Leu Val Ser Glu Arg Gly
1               5

<210> SEQ ID NO 154
<211> LENGTH: 7
<212> TYPE: PRT
```

```
<213> ORGANISM: Artificial Sequence
<220> FEATURE:
<223> OTHER INFORMATION: synthetic enterokinase cleavage sequence

<400> SEQUENCE: 154

Gly Gly Phe Glu Asp Lys Met
1               5

<210> SEQ ID NO 155
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 155

Ser Leu Asp Asp Asp Arg Thr
1               5

<210> SEQ ID NO 156
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 156

Asp Val Tyr Ser Glu Arg Met
1               5

<210> SEQ ID NO 157
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 157

Asn Met Asp Trp Asp Arg Ser
1               5

<210> SEQ ID NO 158
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 158

Ser Leu Asp Asp Asp Arg Thr
1               5

<210> SEQ ID NO 159
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 159

Gly Ser Gly Gly Asp Arg Met
1               5

<210> SEQ ID NO 160
<211> LENGTH: 7
<212> TYPE: PRT
<213> ORGANISM: Artificial Sequence
```

-continued

```
<220> FEATURE:
<223> OTHER INFORMATION: synthetic enterokinase cleavage sequence

<400> SEQUENCE: 160

Phe Ser Glu Glu Asp Arg Met
1               5

<210> SEQ ID NO 161
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 161

Ser Leu Asp Asp Asp Arg Thr
1               5

<210> SEQ ID NO 162
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 162

Val Asp Met His Asp Arg Met
1               5

<210> SEQ ID NO 163
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 163

Ser Gly Gly Asp Asp Arg Met
1               5

<210> SEQ ID NO 164
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 164

Asn Val Arg Met Asp Arg Ser
1               5

<210> SEQ ID NO 165
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 165

Ser His Arg Asp Glu Lys Val
1               5

<210> SEQ ID NO 166
<211> LENGTH: 7
<212> TYPE: PRT
<213> ORGANISM: Artificial Sequence
<220> FEATURE:
```

<223> OTHER INFORMATION: synthetic enterokinase cleavage sequence

<400> SEQUENCE: 166

Leu Met Asn Asp Asp Arg Ala
1               5

<210> SEQ ID NO 167
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 167

Phe Val Met Asn Asp Lys Gly
1               5

<210> SEQ ID NO 168
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 168

Val Ser Asp Asp Asp Arg Ala
1               5

<210> SEQ ID NO 169
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 169

Gly His Val Asp Asp Arg Met
1               5

<210> SEQ ID NO 170
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 170

His Ala Ile Glu Glu Arg Ser
1               5

<210> SEQ ID NO 171
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 171

Asp Ile Asn Asp Asp Arg Ser
1               5

<210> SEQ ID NO 172
<211> LENGTH: 7
<212> TYPE: PRT
<213> ORGANISM: Artificial Sequence
<220> FEATURE:
<223> OTHER INFORMATION: synthetic enterokinase cleavage sequence -continued

```
<400> SEQUENCE: 172

Gly Ser Gly Gly Glu Arg Thr
1               5

<210> SEQ ID NO 173
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 173

Ala Val Ile Gly Asp Arg Ser
1               5

<210> SEQ ID NO 174
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 174

Ser Gly Gly Glu Glu Arg Gly
1               5

<210> SEQ ID NO 175
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 175

Val Glu Phe Tyr Asp Arg Met
1               5

<210> SEQ ID NO 176
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 176

Gly Ser Gly Gly Glu Arg Ile
1               5

<210> SEQ ID NO 177
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 177

Ser Leu Asp Asp Asp Arg Thr
1               5

<210> SEQ ID NO 178
<211> LENGTH: 7
<212> TYPE: PRT
<213> ORGANISM: Artificial Sequence
<220> FEATURE:
<223> OTHER INFORMATION: synthetic enterokinase cleavage sequence
```

```
<400> SEQUENCE: 178

Ser Gly Gly Gln Glu Arg Ser
1               5

<210> SEQ ID NO 179
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 179

Asp Ile Asn Asp Asp Arg Ser
1               5

<210> SEQ ID NO 180
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 180

Asp His Val Trp Asp Arg Ala
1               5

<210> SEQ ID NO 181
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 181

Gly Ser Gly Gly Asp Arg Ile
1               5

<210> SEQ ID NO 182
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 182

Ile Glu Asp Glu Asp Arg Ala
1               5

<210> SEQ ID NO 183
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 183

Met Thr Phe Asp Glu Arg Gly
1               5

<210> SEQ ID NO 184
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 184
```

Gly Asp Trp Asp Asp Lys Asn
1               5

<210> SEQ ID NO 185
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 185

Ile Ala Tyr Gln Asp Arg Met
1               5

<210> SEQ ID NO 186
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 186

Gly Ser Gly Gly Asp Arg Ile
1               5

<210> SEQ ID NO 187
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 187

Gly Phe Val Gln Glu Arg Met
1               5

<210> SEQ ID NO 188
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 188

Asp Ile Asn Asp Asp Arg Ser
1               5

<210> SEQ ID NO 189
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 189

Gly Trp Asn Asp Asp Arg Ile
1               5

<210> SEQ ID NO 190
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 190

```
Gly Gly Phe Glu Asp Arg Leu
1               5
```

<210> SEQ ID NO 191
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 191

```
Gly Ser Gly Gly Asp Arg Asn
1               5
```

<210> SEQ ID NO 192
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 192

```
Ala Ala Val Glu Asp Arg Asn
1               5
```

<210> SEQ ID NO 193
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 193

```
Asp Tyr Arg Leu Asp Arg Ile
1               5
```

<210> SEQ ID NO 194
<211> LENGTH: 7
<212> TYPE: PRT
<213> ORGANISM: Artificial Sequence
<220> FEATURE:
<223> OTHER INFORMATION: synthetic enterokinase cleavage sequence

<400> SEQUENCE: 194

```
Gly Asp Asp Asp Asp Lys Ile
1               5
```

<210> SEQ ID NO 195
<211> LENGTH: 13
<212> TYPE: PRT
<213> ORGANISM: Artificial Sequence
<220> FEATURE:
<223> OTHER INFORMATION: synthetic enterokinase cleavage sequence

<400> SEQUENCE: 195

```
Asp Arg Met Tyr Gln Leu Asp Lys Thr Gly Phe Met Ile
1               5                   10
```

<210> SEQ ID NO 196
<211> LENGTH: 13
<212> TYPE: PRT
<213> ORGANISM: Artificial Sequence
<220> FEATURE:
<223> OTHER INFORMATION: synthetic enterokinase cleavage sequence

<400> SEQUENCE: 196

```
Ala Val Leu Ser Asn Val Met His Ser Asp Asp Trp Thr
```

-continued

```
1               5                  10

<210> SEQ ID NO 197
<211> LENGTH: 9
<212> TYPE: PRT
<213> ORGANISM: Artificial Sequence
<220> FEATURE:
<223> OTHER INFORMATION: natural enterokinase cleavage sequence

<400> SEQUENCE: 197

Gly Asp Asp Asp Asp Lys Ile Tyr Val
1               5

<210> SEQ ID NO 198
<211> LENGTH: 9
<212> TYPE: PRT
<213> ORGANISM: Artificial Sequence
<220> FEATURE:
<223> OTHER INFORMATION: negative control in EK cleavage experiment

<400> SEQUENCE: 198

Ala Val Leu Ser Asn Val Met Phe Ile
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic enterokinase cleavage sequence

<400> SEQUENCE: 199

Gly Asn Tyr Thr Asp Arg Met Phe Ile
1               5

<210> SEQ ID NO 200
<211> LENGTH: 9
<212> TYPE: PRT
<213> ORGANISM: Artificial Sequence
<220> FEATURE:
<223> OTHER INFORMATION: synthetic enterokinase cleavage sequence

<400> SEQUENCE: 200

Asp Ile Asn Asp Asp Arg Ser Leu Phe
1               5

<210> SEQ ID NO 201
<211> LENGTH: 9
<212> TYPE: PRT
<213> ORGANISM: Artificial Sequence
<220> FEATURE:
<223> OTHER INFORMATION: synthetic enterokinase cleavage sequence

<400> SEQUENCE: 201

Asn Lys Ala Lys Asp Arg Met Phe Ile
1               5

<210> SEQ ID NO 202
<211> LENGTH: 9
<212> TYPE: PRT
<213> ORGANISM: Artificial Sequence
<220> FEATURE:
<223> OTHER INFORMATION: synthetic enterokinase cleavage sequence

<400> SEQUENCE: 202

Gly Asn Tyr Thr Asp Arg Arg Phe Ile
1               5
```

```
<210> SEQ ID NO 203
<211> LENGTH: 9
<212> TYPE: PRT
<213> ORGANISM: Artificial Sequence
<220> FEATURE:
<223> OTHER INFORMATION: commercial synthetic enterokinase cleavage
      substrate

<400> SEQUENCE: 203

Gly Asn Tyr Thr Asp Arg Tyr Phe Ile
1               5

<210> SEQ ID NO 204
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (7)..(7)
<223> OTHER INFORMATION: Xaa is any amino acid

<400> SEQUENCE: 204

Asp Ile Asn Asp Asp Arg Xaa
1               5

<210> SEQ ID NO 205
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (7)..(7)
<223> OTHER INFORMATION: Xaa is any amino acid

<400> SEQUENCE: 205

Gly Asn Tyr Thr Asp Arg Xaa
1               5

<210> SEQ ID NO 206
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (1)..(1)
<223> OTHER INFORMATION: Xaa1 is an optional amino acid which, if
      present, is Ala, Asp, Glu, Phe, Gly, Ile, Asn, Ser, or Val
<221> NAME/KEY: MISC_FEATURE
<222> LOCATION: (2)..(2)
<223> OTHER INFORMATION: Xaa2 is an optional amino acid which, if
      present, is Ala, Asp, Glu, His, Ile, Leu, Met, Gln, or Ser
<221> NAME/KEY: MISC_FEATURE
<222> LOCATION: (3)..(3)
<223> OTHER INFORMATION: Xaa3 is an optional amino acid which, if
      present, is Asp, Glu, Phe, His, Ile, Met, Asn, Pro, Val, or Trp
<221> NAME/KEY: MISC_FEATURE
<222> LOCATION: (4)..(4)
<223> OTHER INFORMATION: Xaa4 is Ala, Asp, Glu, or Thr
<221> NAME/KEY: MISC_FEATURE
<222> LOCATION: (7)..(7)
<223> OTHER INFORMATION: Xaa7 is any amino acid

<400> SEQUENCE: 206

Xaa Xaa Xaa Xaa Asp Arg Xaa
1               5
```

```
<210> SEQ ID NO 207
<211> LENGTH: 7
<212> TYPE: PRT
<213> ORGANISM: Artificial Sequence
<220> FEATURE:
<223> OTHER INFORMATION: synthetic enterokinase cleavage sequence
<221> NAME/KEY: MISC_FEATURE
<222> LOCATION: (1)..(1)
<223> OTHER INFORMATION: Xaa1 is an optional amino acid which, if
      present, is Asp or Glu
<221> NAME/KEY: MISC_FEATURE
<222> LOCATION: (2)..(2)
<223> OTHER INFORMATION: Xaa2 is an optional amino acid which, if
      present, is Val
<221> NAME/KEY: MISC_FEATURE
<222> LOCATION: (3)..(3)
<223> OTHER INFORMATION: Xaa3 is an optional amino acid which, if
      present, is Tyr
<221> NAME/KEY: MISC_FEATURE
<222> LOCATION: (4)..(4)
<223> OTHER INFORMATION: Xaa4 is Asp, Glu or Ser
<221> NAME/KEY: MISC_FEATURE
<222> LOCATION: (7)..(7)
<223> OTHER INFORMATION: Xaa7 is any amino acid

<400> SEQUENCE: 207

Xaa Xaa Xaa Xaa Glu Arg Xaa
1               5

<210> SEQ ID NO 208
<211> LENGTH: 6
<212> TYPE: PRT
<213> ORGANISM: Artificial Sequence
<220> FEATURE:
<223> OTHER INFORMATION: synthetic enterokinase cleavage sequence

<400> SEQUENCE: 208

Asp Ile Asn Asp Asp Arg
1               5

<210> SEQ ID NO 209
<211> LENGTH: 6
<212> TYPE: PRT
<213> ORGANISM: Artificial Sequence
<220> FEATURE:
<223> OTHER INFORMATION: synthetic enterokinase cleavage sequence

<400> SEQUENCE: 209

Gly Asn Tyr Thr Asp Arg
1               5

<210> SEQ ID NO 210
<211> LENGTH: 7
<212> TYPE: PRT
<213> ORGANISM: Artificial Sequence
<220> FEATURE:
<223> OTHER INFORMATION: streptavidin binding sequence

<400> SEQUENCE: 210

Trp His Pro Gln Phe Ser Ser
1               5

<210> SEQ ID NO 211
<211> LENGTH: 10
<212> TYPE: PRT
<213> ORGANISM: Artificial Sequence
<220> FEATURE:
<223> OTHER INFORMATION: steptavidin binding sequence

<400> SEQUENCE: 211
```

```
Pro Cys His Pro Gln Phe Pro Arg Cys Tyr
1               5                  10
```

<210> SEQ ID NO 212
<211> LENGTH: 1272
<212> TYPE: DNA
<213> ORGANISM: Artificial Sequence
<220> FEATURE:
<223> OTHER INFORMATION: Bacteriophage M13mp18

<400> SEQUENCE: 212

```
gtgaaaaaat tattattcgc aattccttta gttgttcctt tctattctca ctccgctgaa      60
actgttgaaa gttgtttagc aaaaccccat acagaaaatt catttactaa cgtctggaaa     120
gacgacaaaa ctttagatcg ttacgctaac tatgagggtt gtctgtggaa tgctacaggc     180
gttgtagttt gtactggtga cgaaactcag tgttacggta catgggttcc tattgggctt     240
gctatccctg aaaatgaggg tggtggctct gagggtggcg gttctgaggg tggcggttct     300
gagggtggcg gtactaaacc tcctgagtac ggtgatacac ctattccggg ctatacttat     360
atcaaccctc tcgacggcac ttatccgcct ggtactgagc aaaacccc gc taatcctaat     420
ccttctcttg aggagtctca gcctcttaat actttcatgt ttcagaataa taggttccga     480
aataggcagg gggcattaac tgtttatacg ggcactgtta ctcaaggcac tgaccccgtt     540
aaaacttatt accagtacac tcctgtatca tcaaaagcca tgtatgacgc ttactggaac     600
ggtaaattca gagactgcgc tttccattct ggctttaatg aagatccatt cgtttgtgaa     660
tatcaaggcc aatcgtctga cctgcctcaa cctcctgtca atgctggcgg cggctctggt     720
ggtggttctg gtggcggctc tgagggtggt ggctctgagg gtggcggttc tgagggtggc     780
ggctctgagg gaggcggttc cggtggtggc tctggttccg gtgattttga ttatgaaaag     840
atggcaaacg ctaataaggg ggctatgacc gaaaatgccg atgaaaacgc gctacagtct     900
gacgctaaag gcaaacttga ttctgtcgct actgattacg gtgctgctat cgatggtttc     960
attggtgacg tttccggcct tgctaatggt aatggtgcta ctggtgattt tgctggctct    1020
aattcccaaa tggctcaagt cggtgacggt gataattcac ctttaatgaa taatttccgt    1080
caatatttac cttccctccc tcaatcggtt gaatgtcgcc cttttgtctt tagcgctggt    1140
aaaccatatg aattttctat tgattgtgac aaaataaact tattccgtgg tgtctttgcg    1200
tttcttttat atgttgccac ctttatgtat gtattttcta cgtttgctaa catactgcgt    1260
aataaggagt ct                                                        1272
```

<210> SEQ ID NO 213
<211> LENGTH: 424
<212> TYPE: PRT
<213> ORGANISM: Artificial Sequence
<220> FEATURE:
<223> OTHER INFORMATION: Bacteriophage M13mp18

<400> SEQUENCE: 213

```
Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
                20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Val Cys
        50                  55                  60
```

-continued

```
Thr Gly Asp Glu Thr Gln Cys Tyr Gly Thr Trp Val Pro Ile Gly Leu
 65                  70                  75                  80

Ala Ile Pro Glu Asn Glu Gly Gly Ser Glu Gly Gly Ser Glu
                 85                  90                  95

Gly Gly Gly Ser Glu Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
            195                 200                 205

His Ser Gly Phe Asn Glu Asp Pro Phe Val Cys Glu Tyr Gln Gly Gln
    210                 215                 220

Ser Ser Asp Leu Pro Gln Pro Val Asn Ala Gly Gly Ser Gly
225                 230                 235                 240

Gly Gly Ser Gly Gly Ser Glu Gly Gly Ser Glu Gly Gly
            245                 250                 255

Ser Glu Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
    275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
    355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
                420
```

<210> SEQ ID NO 214
<211> LENGTH: 957
<212> TYPE: DNA
<213> ORGANISM: Artificial Sequence
<220> FEATURE:
<223> OTHER INFORMATION: Bacteriophage M13mp18

<400> SEQUENCE: 214

-continued

```
aaacctcctg agtacggtga tacacctatt ccgggctata cttatatcaa ccctctcgac    60
ggcacttatc cgcctggtac tgagcaaaac cccgctaatc ctaatccttc tcttgaggag   120
tctcagcctc ttaatacttt catgtttcag aataataggt tccgaaatag cagggggca    180
ttaactgttt atacgggcac tgttactcaa ggcactgacc ccgttaaaac ttattaccag   240
tacactcctg tatcatcaaa agccatgtat gacgcttact ggaacggtaa attcagagac   300
tgcgctttcc attctggctt taatgaagat ccattcgttt gtgaatatca aggccaatcg   360
tctgacctgc ctcaacctcc tgtcaatgct ggcggcggct ctggtggtgg ttctggtggc   420
ggctctgagg gtggtggctc tgagggtggc ggttctgagg gtggcggctc tgagggaggc   480
ggttccggtg gtggctctgg ttccggtgat tttgattatg aaagatggc aaacgctaat    540
aagggggcta tgaccgaaaa tgccgatgaa acgcgctac agtctgacgc taaaggcaaa    600
cttgattctg tcgctactga ttacggtgct gctatcgatg gtttcattgg tgacgtttcc   660
ggccttgcta tggtaatgg tgctactggt gattttgctg gctctaattc ccaaatggct    720
caagtcggtg acggtgataa ttcaccttta atgaataatt ccgtcaata tttaccttcc    780
ctcccctcaat cggttgaatg tcgcccttt gtctttagcg ctggtaaacc atatgaattt   840
tctattgatt gtgacaaaat aaacttattc cgtggtgtct ttgcgtttct tttatatgtt   900
gccaccttta tgtatgtatt ttctacgttt gctaacatac tgcgtaataa ggagtct     957
```

```
<210> SEQ ID NO 215
<211> LENGTH: 319
<212> TYPE: PRT
<213> ORGANISM: Artificial Sequence
<220> FEATURE:
<223> OTHER INFORMATION: Bacteriophage M13mp18

<400> SEQUENCE: 215
```

Lys Pro Pro Glu Tyr Gly Asp Thr Pro Ile Pro Gly Tyr Thr Tyr Ile
1               5                   10                  15

Asn Pro Leu Asp Gly Thr Tyr Pro Pro Gly Thr Glu Gln Asn Pro Ala
            20                  25                  30

Asn Pro Asn Pro Ser Leu Glu Glu Ser Gln Pro Leu Asn Thr Phe Met
        35                  40                  45

Phe Gln Asn Asn Arg Phe Arg Asn Arg Gln Gly Ala Leu Thr Val Tyr
    50                  55                  60

Thr Gly Thr Val Thr Gln Gly Thr Asp Pro Val Lys Thr Tyr Tyr Gln
65                  70                  75                  80

Tyr Thr Pro Val Ser Ser Lys Ala Met Tyr Asp Ala Tyr Trp Asn Gly
                85                  90                  95

Lys Phe Arg Asp Cys Ala Phe His Ser Gly Phe Asn Glu Asp Pro Phe
            100                 105                 110

Val Cys Glu Tyr Gln Gly Gln Ser Ser Asp Leu Pro Gln Pro Pro Val
        115                 120                 125

Asn Ala Gly Gly Gly Ser Gly Gly Gly Ser Gly Gly Gly Ser Glu Gly
    130                 135                 140

Gly Gly Ser Glu Gly Gly Gly Ser Glu Gly Gly Gly Ser Glu Gly Gly
145                 150                 155                 160

Gly Ser Gly Gly Gly Ser Gly Gly Asp Phe Asp Tyr Glu Lys Met
                165                 170                 175

Ala Asn Ala Asn Lys Gly Ala Met Thr Glu Asn Ala Asp Glu Asn Ala
            180                 185                 190

Leu Gln Ser Asp Ala Lys Gly Lys Leu Asp Ser Val Ala Thr Asp Tyr

-continued

```
                    195                 200                 205
Gly Ala Ala Ile Asp Gly Phe Ile Gly Asp Val Ser Gly Leu Ala Asn
    210                 215                 220

Gly Asn Gly Ala Thr Gly Asp Phe Ala Gly Ser Asn Ser Gln Met Ala
225                 230                 235                 240

Gln Val Gly Asp Gly Asp Asn Ser Pro Leu Met Asn Asn Phe Arg Gln
                245                 250                 255

Tyr Leu Pro Ser Leu Pro Gln Ser Val Glu Cys Arg Pro Phe Val Phe
            260                 265                 270

Ser Ala Gly Lys Pro Tyr Glu Phe Ser Ile Asp Cys Asp Lys Ile Asn
        275                 280                 285

Leu Phe Arg Gly Val Phe Ala Phe Leu Leu Tyr Val Ala Thr Phe Met
    290                 295                 300

Tyr Val Phe Ser Thr Phe Ala Asn Ile Leu Arg Asn Lys Glu Ser
305                 310                 315
```

<210> SEQ ID NO 216
<211> LENGTH: 450
<212> TYPE: DNA
<213> ORGANISM: Artificial Sequence
<220> FEATURE:
<223> OTHER INFORMATION: Bacteriophage M13mp18

<400> SEQUENCE: 216

```
gattttgatt atgaaaagat ggcaaacgct aataagggg ctatgaccga aaatgccgat      60
gaaaacgcgc tacagtctga cgctaaaggc aaacttgatt ctgtcgctac tgattacggt     120
gctgctatcg atggtttcat tggtgacgtt ccggccttg ctaatggtaa tggtgctact     180
ggtgattttg ctggctctaa ttcccaaatg gctcaagtcg gtgacggtga taattcacct     240
ttaatgaata atttccgtca atatttacct tccctccctc aatcggttga atgtcgccct     300
tttgtcttta gcgctggtaa accatatgaa ttttctattg attgtgacaa aataaactta     360
ttccgtggtg tctttgcgtt tcttttatat gttgccacct ttatgtatgt attttctacg     420
tttgctaaca tactgcgtaa taaggagtct                                       450
```

<210> SEQ ID NO 217
<211> LENGTH: 150
<212> TYPE: PRT
<213> ORGANISM: Artificial Sequence
<220> FEATURE:
<223> OTHER INFORMATION: Bacteriophage M13mp18

<400> SEQUENCE: 217

```
Asp Phe Asp Tyr Glu Lys Met Ala Asn Ala Asn Lys Gly Ala Met Thr
1               5                   10                  15

Glu Asn Ala Asp Glu Asn Ala Leu Gln Ser Asp Ala Lys Gly Lys Leu
            20                  25                  30

Asp Ser Val Ala Thr Asp Tyr Gly Ala Ala Ile Asp Gly Phe Ile Gly
        35                  40                  45

Asp Val Ser Gly Leu Ala Asn Gly Asn Gly Ala Thr Gly Asp Phe Ala
    50                  55                  60

Gly Ser Asn Ser Gln Met Ala Gln Val Gly Asp Gly Asp Asn Ser Pro
65                  70                  75                  80

Leu Met Asn Asn Phe Arg Gln Tyr Leu Pro Ser Leu Pro Gln Ser Val
                85                  90                  95

Glu Cys Arg Pro Phe Val Phe Ser Ala Gly Lys Pro Tyr Glu Phe Ser
            100                 105                 110
```

```
Ile Asp Cys Asp Lys Ile Asn Leu Phe Arg Gly Val Phe Ala Phe Leu
        115                 120                 125

Leu Tyr Val Ala Thr Phe Met Tyr Val Phe Ser Thr Phe Ala Asn Ile
    130                 135                 140

Leu Arg Asn Lys Glu Ser
145                 150
```

ENTEROKINASE CLEAVAGE SEQUENCES

CROSS-REFERENCE TO RELATED APPLICATION

This application claims benefit under 35 U.S.C. §119(e) of Ser. No. 09/597,321, filed Jun. 19, 2000, and converted to a provisional application U.S. No. 60/367,345.

GOVERNMENT FUNDING

The present invention was developed in part with funding under the National Institute of Standards Advanced Technology Program, Cooperative Agreement No. 70NANB7H3057. The government retains certain rights in this invention as a result.

FIELD OF THE INVENTION

The present invention relates to the discovery and use of novel enterokinase recognition sequences. The present invention also relates to the construction and expression from a host cell of a fusion protein comprising a ligand recognition sequence, a novel enterokinase recognition sequence and a protein of interest. Also disclosed is a method for utilizing the ligand and enterokinase recognition sequences to isolate a highly purified protein of interest from the fusion construct by a simple one step procedure involving the incubation of enterokinase enzyme with the fusion protein immobilized on a solid support.

BACKGROUND

The serine protease enterokinase (EK), also known as enteropeptidase, is a heterodimeric glycoprotein present in the duodenal and jejunal mucosa and is involved in the digestion of dietary proteins. Specifically, enterokinase catalyzes the conversion, in the duodenal lumen, of trypsinogen into active trypsin via the cleavage of the acidic propeptide from trypsinogen. The activation of trypsin initiates a cascade of proteolytic reactions leading to the activation of many pancreatic zymogens. (Antonowicz, *Ciba Found. Symp.*, 70: 169–187 (1979); Kitamoto et al., *Proc. Natl. Acad. Sci. USA*, 91(16): 7588–7592 (1994)). EK is highly specific for the substrate sequence $(Asp)_4$-Lys-Ile on the trypsinogen molecule, where it acts to mediate cleavage of the Lys-Ile bond.

EK isolated from bovine duodenal mucosa exhibits a molecular weight (MW) of 150,000 and a carbohydrate content of 35%. The enzyme is comprised of a heavy chain (MW ~115,000) and a disulfide-linked light chain (MW~35,000). (Liepnieks et al., *J. Biol. Chem.*, 254(5): 1677–1683 (1979)). Kitamoto et al., supra, reported that the enterokinase isolated from different organisms exhibits a heavy chain molecular weight variability of from 82–140 kDa and a light chain variability of from 35–62 kDa, depending on the organism. The heavy chain functions to anchor the enzyme in the intestinal brush border membrane and the light chain is the catalytic subunit.

The cloning and functional expression of a cDNA encoding the light chain of bovine enterokinase has been reported. (LaVallie et al., *J. Biol. Chem.*, 268(31): 23311–23317 (1993)). The cDNA sequence codes for a 235 amino acid protein that is highly homologous with a variety of mammalian serine proteases involved in digestion, coagulation and fibrinolysis. The cDNA light chain product migrates at MW 43,000 Da on SDS-PAGE, and exhibits high levels of activity in cleaving the EK-specific fluorogenic substrate Gly-$(Asp)_4$-Lys-beta-naphthylamide.

U.S. Pat. No. 5,665,566 to LaVallie describes the cloning and expression of the enterokinase light chain in CHO cells and Vozza et al., *Biotechnology* (NY), 14(1): 77–81 (1996) describe the production of $rEK_L$ from an expression vector transformed in the methylotrophic yeast *Pichia pastoris*.

Lu et al., *J. Biol. Chem.*, 272(50): 31293–31300 (1997) reported that, while the enterokinase light chain, either produced recombinantly or by partial reduction of purified bovine enteropeptidase, had normal activity toward small peptides with the $(Asp)_4$-Lys sequence, the light chain alone had dramatically reduced activity toward trypsinogen compared to the enteropeptidase holoenzyme. Therefore, the recognition of small substrates requires only the light chain, whereas efficient cleavage of trypsinogen may also depend on the presence of the heavy chain. It has been suggested that the improved ability of the light chain alone to cleave the $(Asp)_4$-Lys sequence in fusion proteins with greater efficiency than the holoenzyme may be due to its ability to easily access the pentapeptide depending on its location within the folded fusion protein.

Collins-Racie et al., *Biotechnology*, 13(9): 982–987 (1995), reported the use of the $(Asp)_4$-Lys pentapeptide substrate in a fusion protein as an autocatalytic substrate for the production of recombinant light chain enterokinase ($rEK_L$). Essentially, $rEK_L$ cDNA was fused in frame to the C-terminus of the coding sequence for *E. coli* DsbA protein, which directs secretion to the *E. coli* periplasmic space. These two domains were joined by the $(Asp)_4$-Lys linker/cleavage sequence fused immediately upstream to the N-terminus of the mature $rEK_L$ domain. Collins-Racie et al. recovered a soluble DsbA/$rEK_L$ fusion protein from cells expressing the gene fusion construct. Following partial purification of the fusion protein, active $rEK_L$ was recovered subsequent to autocatalysis of the $(Asp)_4$-Lys pentapeptide.

Wang et al., *Biol. Chem. Hoppe Seyler*, 376(11): 681–684 (1995) describe the production of enzymatically active recombinant human chymase (rHC), a proteinase present in mast cells, by a method involving proteolytic activation from a ubiquitin fusion protein containing the enterokinase cleavage site in place of the native chymase propeptide. Wang et al. transformed *E. coli* with an expression vector comprising the coding sequence for ubiquitin linked to the enterokinase cleavage sequence linked to the chymase gene. The fusion protein was expressed and analyzed for enterokinase-mediated activation of chymase from the refolded fusion protein. At the highest concentration of enterokinase, approximately 2.5% of the folded fusion protein was converted into enzymatically active rHC, as evidenced in comparative studies with human chymase. From these analyses, Wang et al. concluded that the use of the enterokinase cleavage site in place of the native propeptide for activation purposes, demonstrates that the presence of the native propeptide is not essential for the folding and activation of HC expressed in recombinant systems.

Light et al., *Anal. Biochem.*, 106: 199–206 (1980) investigated the specificity of the enterokinase holoenzyme purified to homogeneity from bovine intestinal mucosa through incubation of the enzyme with various proteins of known sequence followed by an analysis of the resulting fragments on SDS-PAGE. Analysis of the resulting protein fragments indicated that either lysine or arginine can occupy the amino acid position immediately upstream (towards the amino-terminus) of the cleaved peptide bond (the $P_1$ position), an acidic amino acid must occur immediately upstream of this lysine or arginine (the $P_2$ position) and hydrolysis was increased when an acidic amino acid occurred at the $2^{nd}$ and $3^{rd}$ amino acids upstream from the cleaved peptide bond (the $P_2$ and $P_3$ positions).

Additionally, Light and Janska, *Trends Biochem. Sci.*, 14(3) 110–112 (1989), reported studies showing that lysyl, arginyl, or the cysteinyl derivative, S-aminoethyl cysteine, could be substituted for the basic lysine residue and that aspartyl, glutamyl, or S-carboxymethyl cysteine could be substituted for the basic arginine residues. Additionally, they reported that asparagine at the $3^{rd}$ amino acid position upstream from the cleaved peptide bond (known as the "scissile bond") slowed hydrolysis by enterokinase and that changes at the $4^{th}$ and $5^{th}$ upstream positions showed greater variability but also slowed the rate of hydrolysis.

Presently, while current investigations into the advantages of utilizing the highly specific $(Asp)_4$-Lys enterokinase recognition sequence for various chemical and biological applications are promising, these potential applications are hindered by the enzyme/substrate kinetics which act to limit specificity and rate of hydrolysis. Therefore, since enterokinase, both natural and recombinant, is readily available in commercial quantities, it would be advantageous to identify additional enterokinase cleavage sequences that exhibit an even higher specificity as well as a higher rate of hydrolysis than currently observed with the $(Asp)_4$-Lys pentapeptide recognition sequence.

In particular, the discovery of new peptides that are cleaved rapidly and specifically by enterokinase would find beneficial use in the field of large scale protein purification.

SUMMARY OF THE INVENTION

Accordingly, it is an object of the present invention to identify novel enterokinase recognition sequences. Using phage display technology, a number of novel enterokinase recognition sequences have been discovered that provide a highly specific substrate for rapid cleavage by enterokinase. In addition, based on analysis of isolated sequence data, the present invention also discloses the chemical synthesis of short peptides with improved specificity and rate of cleavage at the scissile bond over the initial sequence isolates. These short peptide sequences are about 5–10 amino acids long, more preferably 5–9 amino acids long, and most preferably 5 or 6 amino acids long. The novel enterokinase recognition sequences may be incorporated as a fusion partner into a fusion protein construct, fused to a protein of interest, or included in a fusion protein display in a recombinant genetic package, lending enterokinase cleavability to the fusion protein.

Preferred enterokinase recognition sequences of the present invention exhibit not only a high binding specificity for the enterokinase enzyme but also rapid cleavage by the enzyme at a predetermined site within the cleavage recognition domain. Such sequences are useful for the rapid purification of almost any protein of interest expressed from a host cell.

The present invention also provides DNA sequences encoding an enterokinase-cleavable fusion protein comprising a novel enterokinase recognition sequence of the present invention fused to a protein of interest. Additionally, the DNA construct optionally includes a nucleotide sequence encoding a ligand recognition sequence which specifically recognizes and binds to a ligand binding partner, such as, for instance, a streptavidin binding peptide sequence for binding a streptavidin substrate, providing a means for ready capture of the enterokinase-cleavable protein of interest, which can be released by cleavage at the enterokinase recognition sequence to yield pure protein of interest.

The enterokinase recognition sequence, with or without a ligand recognition sequence fused thereto, can be located anywhere along the fusion protein so long as the chosen location is not associated with any negative properties such as impeding or destroying the biological activity of the protein of interest. In addition, the protein of interest may be present as a complete mature protein or a mutant of a protein, such as, for example, a deletion mutant or substitution mutant.

Also provided by the current invention are methods for the isolation and purification of a protein of interest present as one domain of a larger fusion protein. The protein of interest can be easily cleaved from the rest of the fusion protein, preferably by capture of the fusion protein on a solid substrate and subsequent treatment of the immobilized complex with enterokinase. In one embodiment, the fusion protein is secreted from the host cell into a culture medium. The culture medium is passed over a column which contains a ligand binding partner, such as, for instance, streptavidin or biotin, immobilized on a substrate. The ligand recognition sequence of the fusion protein forms a binding complex with the ligand binding partner thereby immobilizing or capturing the fusion protein on the column. Enterokinase is then added to the column to cleave the protein of interest from the captured fusion complex and the protein of interest is released from the fusion protein complex bound to the ligand binding partner. The purified protein of interest is collected in the flow-through supernatant.

In another embodiment, an expression vector comprising a DNA sequence encoding a fusion protein complex comprising a ligand recognition sequence, an enterokinase cleavage sequence and a protein of interest or fragment thereof may be isolated by first transfecting a host cell with the expression vector and incubating under conditions suitable for expression of the fusion protein. Most preferably, the expression vector also will include a suitable secretion signal sequence (e.g., N-terminal to the ligand recognition sequence) to effect secretion of the expression fusion protein into the culture medium.

In a batch purification process, beads coated with a ligand binding partner for the ligand recognition sequence of the fusion protein may be added directly to the culture medium containing the mature fusion protein. The beads, having captured the fusion protein, may be isolated, e.g., by filtration or immobilized in a magnetic field in the case of magnetic beads, and unwanted components of the culture medium removed. To separate the desired protein of interest from the beads and its fusion partners, enterokinase enzyme or active fragment thereof may then be added to contact the beads and incubated with the bound fusion protein. After cleavage of the fusion protein, the beads may be isolated again, and the protein of interest, now cleaved from the bead/ligand binding partner/enterokinase recognition sequence complex, may be collected in purified form.

In another embodiment, the expression vector comprising the DNA sequence encoding the fusion protein may not include a signal sequence for transport of the expressed fusion construct across the cell membrane. In this instance, the host cell may be lysed after expression of the fusion protein and the cellular debris removed from the culture medium by, for instance, filtration or centrifugation, before capture of the fusion protein on a solid substrate and subsequent treatment of the captured protein complex with enterokinase.

Specific enterokinase recognition sequences according to the present invention are shown in Tables 1–4 (infra). From analysis of cleavage data from the enterokinase recognition sequences presented herein, general formulae for two groups of preferred enterokinase sequences can be seen. Such preferred enterokinase recognitions sequences include polypeptides comprising amino acid sequences of the following general formulae:

$Z_1$-Xaa$_1$-Xaa$_2$-Xaa$_3$-Xaa$_4$-Asp-Arg-Xaa$_5$-$Z_2$ (SEQ ID NO:1), (1)

wherein Xaa$_1$ is an optional amino acid residue which, if present, is Ala, Asp, Glu, Phe, Gly, Ile, Asn, Ser, or Val; Xaa$_2$ is an optional amino acid residue which, if present, is Ala, Asp, Glu, His, Ile, Leu, Met, Gln, or Ser; Xaa$_3$ is an optional amino acid residue which, if present, is Asp, Glu, Phe, His, Ile, Met, Asn, Pro, Val, or Trp; Xaa$_4$ is Ala, Asp, Glu, or Thr; and Xaa$_5$ can be any amino acid residue; and wherein $Z_1$ and $Z_2$ are both optional and are, independently, polypeptides of one or more amino acids; or

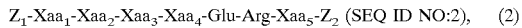

$Z_1$-Xaa$_1$-Xaa$_2$-Xaa$_3$-Xaa$_4$-Glu-Arg-Xaa$_5$-$Z_2$ (SEQ ID NO:2), (2)

wherein Xaa$_1$ is an optional amino acid residue which, if present, is Asp or Glu; Xaa$_2$ is an optional amino acid residue which, if present, is Val; Xaa$_3$ is an optional amino acid residue which, if present, is Tyr; Xaa$_4$ is Asp, Glu, or Ser; and Xaa$_5$ can be any amino acid residue; and wherein $Z_1$ and $Z_2$ are both optional and are, independently, polypeptides of one or more amino acids.

Preferably, in both formulae (1) and (2), above, $Z_1$ will be a polypeptide including a ligand recognition domain or sequence useful for immobilizing the fusion protein of SEQ ID NO:1 by contact with a binding partner for said ligand, and preferably $Z_2$ will be a polypeptide that is or incorporates a protein of interest. Most preferably, the protein of interest will be made up of the polypeptide described by Xaa$_5$-$Z_2$, so that Xaa$_5$ is the N-terminus of the protein of interest, and so that enterokinase cleavage at the scissile bond Arg-Xaa$_5$ liberates the entire protein of interest from the enterokinase recognition sequence and $Z_1$ (if present). Also, preferably, Xaa$_5$ will be Met, Thr, Ser, Ala, Asp, Leu, Phe, Asn, Trp, Ile, Gln, Glu, His, Val, Gly, or Tyr.

An especially preferred group of enterokinase cleavage sequences includes polypeptides comprising the amino acid sequence: Asp-Ile-Asn-Asp-Asp-Arg-Xaa$_5$ (SEQ ID NO:3), wherein Xaa$_5$ can be any amino acid residue, preferably Met, Thr, Ser, Ala, Asp, Leu, Phe, Asn, Trp, Ile, Gln, Glu, His, Val, Gly, or Tyr.

Another group of preferred enterokinase cleavage sequences includes polypeptides comprising the amino acid sequence: Gly-Asn-Tyr-Thr-Asp-Arg-Xaa$_5$ (SEQ ID NO:4), wherein Xaa$_5$ can be any amino acid residue, preferably Met, Thr, Ser, Ala, Asp, Leu, Phe, Asn, Trp, Ile, Gln, Glu, His, Val, Gly, or Tyr.

In a preferred aspect of the present invention, $Z_1$ or $Z_2$ in the formulae (1) and (2) above (SEQ ID NO:1 or 2) will include a modified streptavidin ligand recognition sequence of the formula: Cys-His-Pro-Gln-Phe-Cys (SEQ ID NO:5), and preferably that sequence will be N-terminal to the enterkinase recognition sequence (i.e., will be at least a part of $Z_1$). Inclusion of such sequences will permit the enterokinase recognition sequence, or any polypeptide containing it, to be immobilized on a streptavidin substrate.

In addition, it is also envisioned that the phage display method of the current invention can be used to isolate additional enterokinase recognition sequences as well as optimal substrates for other enzymes of interest.

In another embodiment the present invention provides a fusion protein comprising a protein of interest fused to a ligand recognition sequence via the novel enterokinase recognition sequences of the present invention. The protein of interest can be any protein or fragment thereof capable of expression as a domain in a fusion construct. The fusion construct can be expressed as an intercellular protein in, for instance, *E. coli*, and isolated by disruption of the cells and removal of the fusion construct from the cellular supernatant. Alternatively, the fusion construct can include a peptide signal sequence effective for signaling secretion from the host cell producing the fusion protein. This will preclude the necessity to lyse the *E. coli* or other host cells to release the expressed fusion protein and thereby eliminates the need for an additional protein purification step specifically to remove unwanted cellular debris. Signal peptide sequences that are known to facilitate secretion of peptides expressed in *E. coli* into the culture medium include Pel B, bla, and phoA.

The ligand recognition sequence domain of the fusion construct can be any sequence which recognizes or exhibits an affinity for a binding partner such as, for instance, streptavidin. Preferred recognition sequences include the streptavidin binding sequence His-Pro-Gln-Phe (SEQ ID NO:6) and the modified streptavidin binding sequences Cys-His-Pro-Gln-Phe-Cys (SEQ ID NO:5) and Cys-His-Pro-Gln-Phe-Cys-Ser-Trp-Arg (SEQ ID NO:7). Additional preferred recognition sequences include the streptavidin binding sequences Trp-His-Pro-Gln-Phe-Ser-Ser (SEQ ID NO:210) and Pro-Cys-His-Pro-Gln-Phe-Pro-Arg-Cys-Tyr (SEQ ID NO:211). The addition of the cysteines to the modified streptavidin binding sequence makes the domain somewhat more like a protein (in that the domain obtains a 3-dimensional structure), the addition of tryptophan makes the binding sequence a better UV absorber (therefore making it easier to assay), and the addition of arginine aids solubility. In a preferred embodiment the streptavidin ligand recognition sequence or the modified streptavidin ligand recognition sequence is fused at the amino-terminal end of the novel enterokinase recognition sequences disclosed in the present application. Several such sequences can be added in tandem to provide multimeric immobilization sites.

In another embodiment, the present invention provides a DNA expression vector, for transformation of a host cell, coding for a fusion protein comprising a protein of interest fused at either the NH$_2$-terminus or COOH-terminus to an enterokinase recognition sequence of the present invention. The enterokinase recognition sequence may additionally be fused to a ligand recognition sequence which binds to a particular ligand and can be used to capture the ligand recognition sequence and any protein of interest attached to it, to a solid substrate. Preferably the ligand recognition sequence is positioned relative to the enterokinase recognition sequence and the protein of interest so that upon capture on a solid substrate, treatment of the fusion construct with enterokinase enzyme will release the protein of interest from the construct. Additional DNA sequences included in the expression vector may include a promoter to facilitate expression of the fusion protein in the selected host cell and preferably also a signal sequence to facilitate secretion of the fusion protein into the culture medium prior to the purification step.

In another embodiment, the expression vector does not include a signal sequence directing secretion of the expressed fusion protein into the culture medium. According to this method, after expression of the fusion protein in the host cell, the host cell is lysed and the cellular debris separated from the culture supernatant and the fusion protein by, for instance, filtration, and the protein of interest isolated according to any of the previous methods.

In accordance with the present invention, desired gene products are produced as fusion proteins expressed from host microorganisms, the fusion protein comprising a novel enterokinase cleavage sequence inserted between a ligand recognition sequence and a protein of interest. It has been found that desired peptides or proteins can be obtained in the mature form from fusion proteins produced in the above manner when the latter are treated with enterokinase capable of specifically recognizing and hydrolyzing a peptide bond within the recognition sequence. If necessary, the enterokinase may be used in combination with an aminopeptidase capable of specifically liberating a basic amino acid residue from the N-terminal side of the protein of interest or a carboxypeptidase capable of specifically liberating a basic amino acid residue from the C-terminal side of the protein of interest.

The most preferred fusion protein of the present invention, translated from an expression vector transformed in a host cell, comprises a secretion signal sequence fused to the amino-terminus of a ligand recognition sequence fused to the amino-terminus of a novel enterokinase recognition sequence of the present invention fused at its carboxy-terminus to the amino-terminal end of a protein of interest. The protein of interest may be isolated and rapidly purified in a few easy steps. Essentially, the fusion protein is expressed under suitable conditions in a host system, such as, for instance, *E. coli*. After expression, the fusion protein is secreted from the host cell into the culture medium. The culture medium is then contacted with a ligand binding partner immobilized on a solid substrate under conditions suitable for binding of the ligand recognition sequence to the immobilized ligand binding partner. Treatment of the resulting complex with enterokinase releases the protein of interest from the immobilized fusion complex such that it may be subsequently isolated from the flow-through supernatant in a highly purified, biologically active form.

In another embodiment, the present invention provides a method for rapid purification of a protein of interest comprising:
(a) culturing a host cell transformed with an expression vector encoding a fusion protein comprising the elements: an enterokinase recognition sequence according to the invention, a protein of interest, and a ligand recognition sequence, the elements being expressed as a fusion construct in such a manner that each element is fully functional and no element interferes with the functionality of any other element in the construct;
(b) contacting a sample of the culture medium or cellular extract with a ligand binding partner for said ligand recognition sequence immobilized on a solid substrate;
(c) incubating the sample with enterokinase;
(d) recovering any protein of interest released from step (c). Optionally, one or more wash steps may be included in the purification process.

In another embodiment, the host cell may be lysed and the cellular debris separated from the fusion protein prior to isolation of the protein of interest.

Specific embodiments of the invention include the following:

A polypeptide comprising an enterokinase recognition sequence and having the formula:

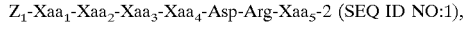
$Z_1$-Xaa$_1$-Xaa$_2$-Xaa$_3$-Xaa$_4$-Asp-Arg-Xaa$_5$-2 (SEQ ID NO:1), wherein Xaa$_1$ is an optional amino acid residue which, if present, is Ala, Asp, Glu, Phe, Gly, Ile, Asn, Ser, or Val; Xaa$_2$ is an optional amino acid residue which, if present, is Ala, Asp, Glu, His, Ile, Leu, Met, Gln, or Ser; Xaa$_3$ is an optional amino acid residue which, if present, is Asp, Glu, Phe, His, Ile, Met, Asn, Pro, Val, or Trp; Xaa$_4$ is Ala, Asp, Glu, or Thr; and Xaa$_5$ can be any amino acid residue; and wherein $Z_1$ and $Z_2$ are both optional and are, independently, polypeptides of one or more amino acids. Preferably Xaa$_1$ is Asp, Xaa$_2$ is Ile, Xaa$_3$ is Asn, Xaa4 is Asp, and Xaa$_5$ is Met, Thr, Ser, Ala, Asp, Leu, Phe, Asn, Trp, Ile, Gln, Glu, His, Val, Gly, or Tyr.

In a particular embodiment, the polypeptide $Z_1$ is a ligand recognition sequence, e.g., a streptavidin binding domain. Specific streptavidin binding domains may be selected from the sequences: His-Pro-Gln-Phe (SEQ ID NO:6), Cys-His-Pro-Gln-Phe-Cys (SEQ ID NO:5), Cys-His-Pro-Gln-Phe-Cys-Ser-Trp-Arg (SEQ ID NO:7), Trp-His-Pro-Gln-Phe-Ser-Ser (SEQ ID NO:210), Pro-Cys-His-Pro-Gln-Phe-Pro-Arg-Cys-Tyr (SEQ ID NO:211), and tandemly arranged combinations and repeats thereof.

In a further embodiment, the polypeptide $Z_2$ is a protein of interest. Preferably, the polypeptide Xaa$_5$-$Z_2$ is a protein of interest, i.e., the polypeptide of SEQ ID NO:1 is a fusion protein which, upon treatment with EK and cleavage of the scissile bond, yields an isolated protein of interest.

Other specific embodiments of the present invention include the following:

A polypeptide comprising an enterokinase recognition sequence and having the formula:

$Z_1$-Xaa$_1$-Xaa$_2$-Xaa$_3$-Xaa$_4$-Glu-Arg-Xaa$_5$-$Z_2$ (SEQ ID NO:2), wherein Xaa$_1$ is an optional amino acid residue which, if present, is Asp or Glu; Xaa$_2$ is an optional amino acid residue which, if present, is Val; Xaa$_3$ is an optional amino acid residue which, if present, is Tyr; Xaa$_4$ is Asp, Glu, or Ser; and Xaa$_5$ can be any amino acid residue; and wherein $Z_1$ and $Z_2$ are both optional and are, independently, polypeptides of one or more amino acids. Preferably Xaa$_5$ is Met, Thr, Ser, Ala, Asp, Leu, Phe, Asn, Trp, Ile, Gln, Glu, His, Val, Gly, or Tyr.

In a particular embodiment, the polypeptide $Z_1$ is a ligand recognition sequence, e.g., a streptavidin binding domain. Specific streptavidin binding domains may be selected from the sequences: His-Pro-Gln-Phe (SEQ ID NO:6), Cys-His-Pro-Gln-Phe-Cys (SEQ ID NO:5), Cys-His-Pro-Gln-Phe-Cys-Ser-Trp-Arg (SEQ ID NO:7), Trp-His-Pro-Gln-Phe-Ser-Ser (SEQ ID NO:210), Pro-Cys-His-Pro-Gln-Phe-Pro-Arg-Cys-Tyr (SEQ ID NO:211),
and tandemly arranged combinations and repeats thereof.

In a further embodiment, the polypeptide $Z_2$ is a protein of interest. Preferably, the polypeptide Xaa$_5$-$Z_2$ is a protein of interest, i.e., the polypeptide of SEQ ID NO:1 is a fusion protein which, upon treatment with EK and cleavage of the scissile bond, yields an isolated protein of interest.

Preferred enterkinase recognition sequences according to the invention may be selected from the group consisting of SEQ ID NOs: 10–73 and 75–193, as shown in Tables 1, 2, 3, and 4 (infra).

In a preferred embodiment, the invention provides a polynucleotide, encoding an enterokinase cleavable fusion protein including the following domains, arranged in the direction of amino-terminus to carboxy-terminus: a ligand recognition sequence, an enterokinase recognition sequence having the formula Asp-Ile-Asn-Asp-Asp-Arg (SEQ ID NO:208) or Gly-Asn-Tyr-Thr-Asp-Arg (SEQ ID NO:209), and a protein of interest. Vectors comprising circular DNA and including said polynucleotide are also contemplated. Expression vectors comprising the polynucleotide operably linked to a promoter sequence for expression in a recombinant host are also contemplated. Expression vectors further comprising a signal sequence operably linked to the polynucleotide, i.e., for effecting secretion of the expressed fusion protein into a culture medium are also contemplated.

Recombinant prokaryotic or eukaryotic host cells transformed with such vectors also are contemplated.

Additional embodiments of the present invention include the following:

A method for isolating a protein of interest comprising: (a) culturing a recombinant host cell expressing a recombinant polynucleotide encoding an enterokinase cleavable fusion protein including the following domains, arranged in the direction of amino-terminus to carboxy-terminus: a ligand recognition sequence, an enterokinase recognition sequence having the formula:

Xaa$_1$-Xaa$_2$-Xaa$_3$-Xaa$_4$-Asp-Arg-Xaa$_5$ (SEQ ID NO:206), wherein Xaa$_1$ is an optional amino acid residue which, if present, is Ala, Asp, Glu, Phe, Gly, Ile, Asn, Ser, or Val; Xaa$_2$ is an optional amino acid residue which, if present, is Ala, Asp, Glu, His, Ile, Leu, Met, Gln, or Ser; Xaa$_3$ is an optional amino acid residue which, if present, is Asp, Glu, Phe, His, Ile, Met, Asn, Pro, Val, or Trp; Xaa$_4$ is Ala, Asp, Glu, or Thr; and Xaa$_5$ can be any amino acid residue; or Xaa$_1$-Xaa$_2$-Xaa$_3$-Xaa$_4$-Glu-Arg-Xaa$_5$ (SEQ ID NO:207), wherein Xaa$_1$ is an optional amino acid residue which, if present, is Asp or Glu; Xaa$_2$ is an optional amino acid residue which, if present, is Val; Xaa$_3$ is an optional amino acid residue which, if present, is Tyr; Xaa$_4$ is Asp, Glu, or Ser; and Xaa$_5$ can be any amino acid residue, and a protein of interest, under conditions suitable for expression of said fusion protein;
(b) contacting the expressed fusion protein with a binding ligand immobilized on a solid support under conditions suitable for formation of a binding complex between the binding ligand and the ligand recognition sequence;
(c) contacting the binding complex with enterokinase; and
(d) recovering the protein of interest.

Where said fusion protein is not secreted on expression, the foregoing method may optionally include the further steps, after step (a), of lysing the host cells and separating the cellular debris from the lysate. Where said fusion protein is secreted on expression, the foregoing method may optionally include the further step of collecting the culture media containing the secreted fusion protein.

In the foregoing method, said fusion protein preferably has the formula:

Z$_1$-Xaa$_1$-Xaa$_2$-Xaa$_3$-Xaa$_4$-Asp-Arg-Xaa$_5$-Z$_2$ (SEQ ID NO:1), wherein Xaa$_1$ is an optional amino acid residue which, if present, is Ala, Asp, Glu, Phe, Gly, Ile, Asn, Ser, or Val; Xaa$_2$ is an optional amino acid residue which, if present, is Ala, Asp, Glu, His, Ile, Leu, Met, Gln, or Ser; Xaa$_3$ is an optional amino acid residue which, if present, is Asp, Glu, Phe, His, Ile, Met, Asn, Pro, Val, or Trp; Xaa$_4$ is Ala, Asp, Glu, or Thr; and Xaa$_5$ can be any amino acid residue; Z$_1$ is a polypeptide comprising the sequence His-Pro-Gln-Phe-Ser-Ser-Pro-Ser-Ala-Ser-Arg-Pro-Ser-Glu-Gly-Pro-Cys-His-Pro-Gln-Phe-Pro-Arg-Cys-Tyr-11e-Glu-Asn-Leu-Asp-Glu-Phe-Ser-Gly-Leu-Thr-Asn-Ile (SEQ ID NO:84), and Xaa$_5$-Z$_2$ is a protein of interest.

In another preferred embodiment of the foregoing method, the fusion protein has the formula: Z$_1$-Xaa$_1$-Xaa$_2$-Xaa$_3$-Xaa$_4$-Glu-Arg-Xaa$_5$-Z$_2$ (SEQ ID NO:2), wherein Xaa$_1$ is an optional amino acid residue which, if present, is Asp or Glu; Xaa$_2$ is an optional amino acid residue which, if present, is Val; Xaa$_3$ is an optional amino acid residue which, if present, is Tyr; Xaa$_4$ is Asp, Glu, or Ser; and Xaa$_5$ can be any amino acid residue; Z$_1$ is a polypeptide comprising the sequence His-Pro-Gln-Phe-Ser-Ser-Pro-Ser-Ala-Ser-Arg-Pro-Ser- Glu-Gly-Pro-Cys-His-Pro-Gln-Phe-Pro-Arg-Cys-Tyr-Ile-Glu-Asn-Leu-Asp-Glu-Phe-Ser-Gly -Leu-Thr-Asn-Ile (SEQ ID NO:84), and Xaa-Z$_5$ is a protein of interest. Most preferably, Xaa$_5$ is Met, Thr, Ser, Ala, Asp, Leu, Phe, Asn, Trp, Ile, Gln, Glu, His, Val, Gly, or Tyr.

In a further embodiment of the present invention, a method is provided for isolating a genetic package of interest comprising the steps:
(a) expressing in a genetic package a fusion protein comprising a protein of interest fused to an enterokinase cleavage sequence fused to a polypeptide expressed on the surface of said genetic package;
(b) contacting the genetic package with a ligand for the protein of interest, which ligand is capable of being immobilized on a solid support, under conditions suitable for the formation of a binding complex between said ligand and said protein of interest;
(c) immobilizing said ligand on a solid support, either before or after said contacting step (b),
(d) contacting the immobilized binding complex formed in step (b) with enterokinase; and
(e) recovering the genetic package of interest from said solid support.

In the foregoing method, the ligand may be immobilized, for example, by biotinylating the ligand and then binding to immobilized steptavidin or avidin. Alternatively, the ligand is immobilized by binding to an immobilized antibody that binds said ligand.

The genetic package is preferably selected from the group consisting of: bacteriophage, bacteria, bacterial spores, yeast cells, yeast spores, insect cells, eukaryotic viruses, and mammalian cells. A genetic package of interest recovered in the foregoing method may be amplified in an appropriate host including but not limited to bacterial cells, insect cells, mammalian cells, and yeast. A preferred genetic package is a filamentous bacteriophage (such as M13-derived phage) and the polypeptide expressed on the surface of said host, i.e., which anchors the fusion protein to the surface of the genetic package, is selected from the group consisting of: gene III protein (SEQ ID NO:213); domain 2:: domain 3:: transmembrane domain:: intracellular domain of gene III protein (SEQ ID NOs:215); and domain 3:: transmembrane domain:: intracellular anchor of gene III protein (SEQ ID NOs:217).

In preferred embodiments, the protein of interest is an antibody or fragment thereof.

The present invention further provides a method for controlling the activity of a protein of interest comprising the steps:
(a) expressing in a recombinant host a fusion protein comprising the elements: (i) a first protein fused to (ii) an enterokinase cleavage sequence fused to (iii) a second protein, wherein said fusion protein has suppressed activity due to the conformation of elements (i), (ii) and (iii);
(b) treating the fusion protein with enterokinase such that said first protein and second protein are separated and at least one of said first protein and said second protein thereby exhibits the activity of a protein of interest.

In one embodiment of the foregoing method, said second protein is the protein of interest and is a protease, and said first protein is an inhibitor of the protease. In another embodiment, said first protein is the protein of interest and is a protease, and said second protein is an inhibitor of the protease. In another embodiment, said first protein is the variable light (V$_L$) domain of an scFv antibody, and said second protein is the variable heavy ($V_H$) domain of an scFv antibody, and wherein said protein of interest is the scFv formed by the association of said first protein with said second protein. In another embodiment, said second protein is the variable light ($V_L$) domain of an scFv antibody, and said first protein is the variable heavy ($V_H$) domain of an scFv antibody, and said protein of interest is the scFv formed by the association of said first protein with said second protein.

The present invention additionally provides a method for detecting the expression of a fusion protein on the surface of a recombinant host comprising the steps:

(a) expressing, in a recombinant host, a fusion protein comprising a first protein fused to an enterokinase cleavage sequence fused to a second protein fused to a polypeptide expressed on the surface of said host;
(b) contacting the host with a ligand for said first protein immobilized on a solid support under conditions suitable for forming a binding complex between the ligand and the first protein;
(c) removing unbound materials;
(d) treating any bound complex with enterokinase;
(e) recovering hosts released from said solid support, wherein said recovered hosts are verified expressors of said fusion protein.

In preferred embodiments, the first protein is a streptavidin-binding polypeptide and said ligand is streptavidin, and the second protein is an antibody or an antibody fragment.

The present invention also provides a method of selecting display polypeptides from a display library that have specific affinity for a target, comprising the steps:

(a) providing a display library of polypeptides comprising a multiplicity of genetic packages, wherein each genetic package expresses a fusion protein that comprises an enterokinase recognition sequence between a diplay polypeptide library member and a polypeptide that anchors the fusion protein to the genetic package,
(b) contacting the display library with a target,
(c) immobilizing the target on a solid support, either before or after said contacting step (b),
(d) separating non-binding genetic packages from bound genetic packages,
(e) treating the bound genetic packages with enterokinase, and
(f) recovering and amplifying the genetic packages released.

Preferably, the genetic package is an M13 phage. More preferably, polypeptide that anchors the fusion protein to the genetic package comprises at least the domain 3:: transmembrane domain:: intracellular domain portion of the gene III protein. In particular embodiments, the display polypeptides exhibited by the genetic packages of the display library comprise human Fabs. In other embodiments, the display polypeptides comprise peptides of, e.g., ten to twenty-one amino acids in length. Specific embodiments include display peptides containing two cysteine residues.

BRIEF DESCRIPTION OF THE DRAWINGS

FIG. 1 shows enterokinase cleavage using 30 nM recombinant light chain enterokinase (Novagen); FIG. 2 shows enterokinase cleavage using 130 nM recombinant light chain enterokinase.

DEFINITIONS

Figure 1:
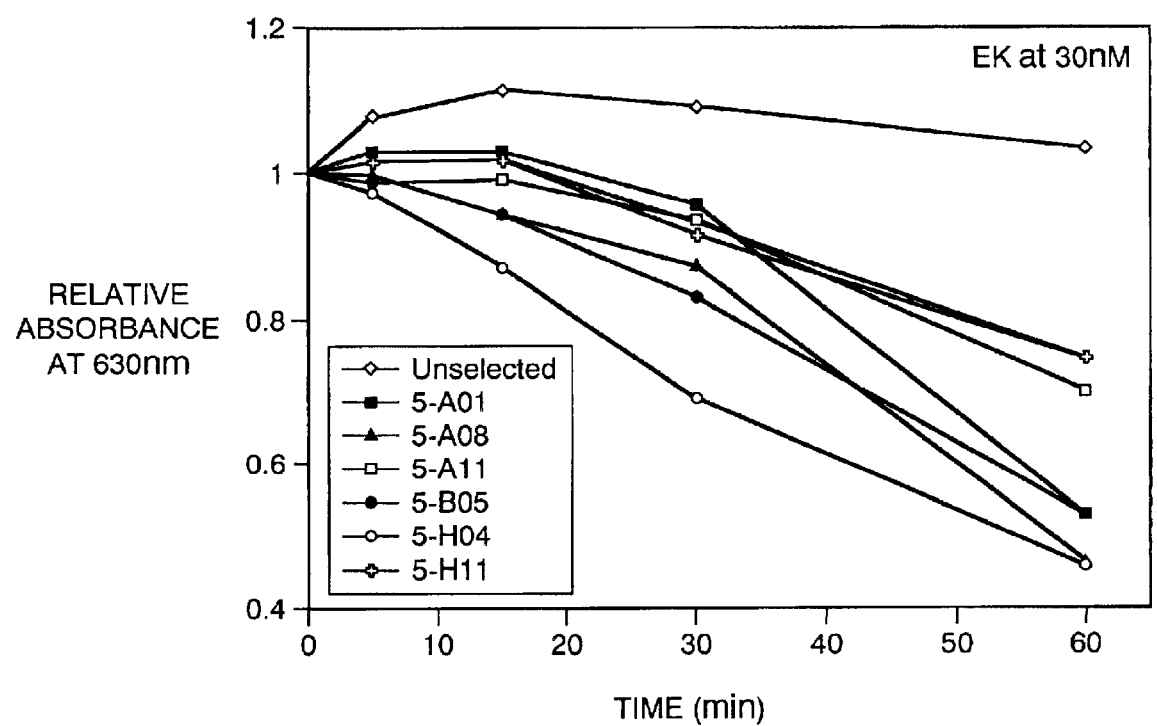
FIG. 1 and FIG. 2 show the time course of enterokinase cleavage of phage isolates from five rounds of screening a substrate phage library. The tested isolates were those having recurring sequences among 90 sequenced isolates. The isolates are tested in comparison with an isolate (5-H11) containing the known enterokinase cleavage sequence DDDDK and an unselected phage displaying a polypeptide not recognized by enterokinase.

As used herein, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompases DNA molecules which have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage", as used herein, is defined as a bacterial virus containing a DNA core and a protective shell built up by the aggregation of a number of different protein molecules. The term "Ff phage", as used herein, denotes phage selected from the set comprising M13, f1, and fd and their recombinant derivatives. The term "filamentous phage", as used herein denotes the phage selected from the set comprising Ff phage, IKe, Pf1, Pf3, and other related phage known in the art. Bacteriophage include filamentous phage, phage lambda, T1, T7, T4, and the like. The terms "bacteriophage" and "phage" are used herein interchangeably. Unless otherwise noted, the terms "bacteriophage" and "phage" also encompass "phagemids", i.e., plasmids which contain the packaging signals of filamentous phage such that infectious phage-like particles containing the phagemid genome can be produced by coinfection of the host cells with a helper phage. A particularly useful phage for the isolation of enterokinase cleavage sequences of the invention via phage display technology is the recombinant, single-stranded DNA, filamentous M13 phage and its derivatives. In the present application, reference to "an M13 phage" encompasses both M13 phage (wild-type) and phage derived from M13 phage (i.e., "M13-derived phage"). Such M13-derived phage contain DNA that encodes all the polypeptides of wild type M13 phage and which can infect $F^+$ $E.$ $coli$ to produce infectious phage particles. M13-derived phage, in other words, include functional versions of all of the wild-type M13 genes. The native M13 genes may have been altered in M13-derived phage, for various purposes familiar to those in the art, e.g., incorporation of silent mutations, truncations of native genes that do not affect viability or infectivity of the phage, removal or insertion of restriction sites, or addition of non-native genes into intergenic regions of the M13 genome. The term "an M13 phage" specifically includes such phage as M13 mp18, M13 mp7, M13 mp8, M13 mp9. See, U.S. Pat. No. 5,233,409; U.S. Pat. No. 5,403,484; U.S. Pat. No. 5,571,698, all incorporated herein by reference.

The term "genetic package", as used herein, denotes a package that contains a genetic message encoding at least one protein that, in suitable circumstances, assembles into the package and is at least partly exposed on the package surface. Genetic packages include bacteriophages, bacterial cells, spores, eukaryotic viruses, and eukaryotic cells.

The term "host", as used herein, denotes a cell type in which genetic packages can be grown. Hosts include bacterial cells, insect cells, mammalian cells, and yeast. Some genetic packages are their own hosts, such as yeast and bacterial cells. For viral genetic packages, a separate host cell is required. Suitable hosts for filamentous phage are gram negative bacteria, such as $E.$ $coli.$ A suitable host for baculovirus is insect cells (see, Ojala, et al., $Biochem.$ $Biophys.$ $Res.$ $Commun.$, 284(3):777–84 (2001)).

The term "enterokinase" as used herein is a pancreatic hydrolase which facilitates the cleavage and activation of trypsinogen into trypsin as part of the catalytic cascade involved in the digestive process. "Enterokinase" includes both the native enzyme isolated from any source as well as the enzyme produced by recombinant techniques. The enterokinase described herein may exist as a dimer comprising a disulfide-linked heavy chain of approximately 120 kDa and a light chain of approximately 47 kDa. Alternatively, the light chain alone, which contains the catalytic domain, may be used. The light chain may be isolated from a native source or produced recombinantly.

The term "enterokinase recognition sequence" as used herein, denotes those sequences, usually a short polypeptide of fewer than 30 amino acids, which are contacted and cleaved by the enterokinase enzyme. The terms "enterokinase recognition sequence" and "enterokinase cleavage sequence" are used herein interchangeably.

The term "enterokinase recognition domain" as used herein, denotes the complete sequence of amino acids which must be present in order for the enterokinase enzyme to recognize and cleave a specific site within the "enterokinase recognition domain", regardless of whether those sequences come in direct physical contact with the enzyme or are in close proximity to the actual site of cleavage.

The term "scissile bond" as used herein, denotes the specific peptide bond joining consecutive amino acids via an amide linkage that is cleaved by the enterokinase enzyme. By standard nomenclature, the scissile bond occurs between the $P_1$ and $P_1'$ amino acids within the enterokinase recognition sequence.

The term "ligand recognition sequence" as used herein, denotes a sequence of amino acids recognizing, that is, binding to, a known ligand or binding partner. If utilized in the process of isolating and purifying a protein or protein fragment, it is desirable for the ligand recognition sequence to exhibit a high specificity and high affinity for the ligand or binding partner. Examples of a ligand recognition sequence would include streptavidin (or avidin), which would recognize a biotin binding partner, or a streptavidin binding sequence (see, e.g., SEQ ID NO:5), which would form a binding complex with a streptavidin binding partner. Other examples of ligand binding partners include antibodies raised against a specific peptide antigen, which peptide antigen would be suitable for use as a ligand recognition sequence. Other examples of specific ligand recognition sequences include the Myc-tag (Munro & Pelham, *Cell*, 46: 291–300 (1986); Ward et al., *Nature*, 341: 544–546 (1989), the Flag peptide (Hopp et al., *BioTechnology*, 6: 1204–1210 (1988), the KT3 epitope peptide (Martin et al., *Cell*, 63: 843–849 (1990); Martin et al., *Science*, 255: 192–194 (1992), an α-tubulin epitope peptide (Skinner et al., *J. Biol. Chem.*, 266: 14163–14166 (1991), polyhistidine tags (esp. hexahistidine tails), chitin binding domain (CBD), maltose binding protein (MBP), and the T7 gene 10-protein peptide tag (Lutz-Freyermuth et al., *Proc. Natl. Acad. Sci. USA*, 87: 6393–6397 (1990), all of which have been used successfully for the detection and in some cases also for the purification of a recombinant gene product.

The term "fusion protein" as used herein, denotes a polypeptide formed by expression of a hybrid gene made by combining more than one gene sequence. Typically a fusion protein is produced by cloning a cDNA into an expression vector in-frame with an existing gene.

The term "protein of interest" as used herein, denotes any protein, fragment thereof, or polypeptide of any length which may be isolated and purified from its native source, or produced by recombinant DNA techniques and expressed from its native source or from a recombinant host cell, or produced by any chemical synthesis method.

The term "display library", as used herein, denotes a plurality of genetic packages that differ only in the protein or peptide displayed. The displayed protein or peptide can be highly homologous in parts and variable in other parts, such as in a display library of Fabs. A library of displayed peptides may show no internal homology other than length and common flanking sequences or might have fixed internal amino acids, such as cysteines. A display library may also comprise a collection of cDNAs from a given cell type all fused to the same anchor protein and displayed on the same genetic package.

DETAILED DESCRIPTION

The present invention provides novel, highly specific and rapidly cleaved enterokinase recognition sequences. The novel enterokinase recognition sequences of the present invention are small polypeptides of three or more residues which provide a substrate specifically recognized and cleaved by recombinant light chain enterokinase.

The present invention also contemplates a DNA sequence encoding an enterokinase cleavage sequence according to the present invention, preferably as part of an expression vector for transformation of a host cell and expression of a protein of interest. The expression vector preferably includes a DNA sequence that encodes a fusion protein, the fusion protein comprising several domains including, preferably, a signal sequence, a ligand recognition sequence, a novel enterokinase cleavage sequence and a protein of interest. Optionally, a fusion protein lacking a signal sequence is also envisioned by the present application.

Using standard recombinant DNA techniques, a host cell is transformed with the expression vector and under appropriate conditions, the fusion protein is expressed by the host cell. The signal sequence is desirable to facilitate secretion of the protein of interest into the culture medium prior to isolation and purification of the protein of interest. This avoids the potential problem of degradation of the protein of interest in the host cell and avoids the requirement for lysis of the host cell in turn resulting in contamination of the cell medium with unwanted proteins and other cellular debris present in a whole cell lysate. By this method, the protein of interest may be purified directly from the culture medium without the necessity of additional purification steps to remove unwanted products. However, purification of a non-secreted protein after cell lysis is also envisioned by the methods of the present invention. For instance, a protein of interest lacking a signal sequence may be purified from a fusion construct that includes a novel enterokinase cleavage sequence according to the present invention by methods described herein.

The present invention also describes construction of a cassette for expression and rapid purification of a protein of interest. Using the described cassette, virtually any protein of interest can be fused either at its $NH_2$-terminal or COOH-terminal end to the novel enterokinase cleavage sequences of the current invention. A purified protein of interest is easily obtained as seen by the examples described below.

As previously described, the present invention may be used to isolate and purify any number of proteins of interest. By knowing every amino acid which may occur at the $P_1'$ position of the enterokinase recognition domain, it can be determined if the first amino acid (occurring at either the NH₂-terminal or COOH-terminal end) of a protein of interest may be fused in a construct to the $P_1$ amino acid. If this first amino acid of the protein to be purified is allowed at the $P_1'$ position, treatment with enterokinase to remove the $P_n$-$P_1$ amino acids allows for the immediate isolation of a purified protein directly from the purification eluate. As used herein $P_n$-$P_1$ designates those amino acids which are part of the enterokinase recognition domain and occur to the amino-terminal side of the protein of interest. However, even if the first amino acid of the protein of interest must be fused "downstream" of the $P_1'$ position, i.e., $P_2'$, P3' etc., a highly purified protein may still be isolated from the purification eluate and the only subsequent purification step necessary is the removal of any undesired terminal amino acids from the purified protein. In many cases the extra amino acid(s) can remain attached to the protein of interest with no effect on biological activity, hence a subsequent purification/cleavage step is unnecessary.

The novel enterokinase recognition sequences of the present invention may also be used for release of a protein of interest, including without limitation an antibody or fragment thereof, that is expressed as a display on the surface of a genetic package. Following expression and display of a fusion construct that includes a surface protein or portion (stump) of a surface protein, linked to an enterokinase recognition sequence, linked to the protein of interest on the surface of the genetic package, treatment of the culture containing the genetic package or of purified genetic package with enterokinase will release the protein of interest from the fusion protein construct. According to this method, the fusion protein display on the genetic package comprises the protein of interest fused at its N-terminus or C-terminus (preferably the N-terminus) of an enterokinase recognition sequence of the present invention, and the other end (preferably the C-terminus) of the enterokinase recognition sequence is fused to a protein or portion thereof expressed on the surface of the genetic package. The host cell for display of the fusion may be any suitable cell, including without limitation bacterial cells, yeast cells, bacterial spores, or yeast spores, insect cells, or mammalian cells.

Following incubation with enterokinase, the released genetic package of interest may be collected and amplified using methods well known in the art. For example, F+ *E coli* cells can be infected with Ff phage so released.

In a preferred embodiment, a phage host will display a fusion protein including a protein of interest such as an antibody or a functional fragment thereof (e.g., Fab fragment, scFv, Fv, etc.) fused to an enterokinase recognition sequence of the invention, fused to a phage surface protein or portion thereof. Most preferably the fusion protein is expressed in an M13 phage. The phage surface protein used may be, e.g., the complete gene III protein of M13 filamentous bacteriophage (SEQ ID NO:213); domain 2, domain 3, the transmembrane domain, and the intracellular anchor domaim of gene III protein (SEQ ID NOs:215); domain 3 of gene III, the transmembrane domain, and the intracellular anchor domain of protein (SEQ ID NOs:217), mature gene VIII protein of a filamentous bacteriophage, or any varied, modified, truncated, or mutated form of these proteins which may be stably expressed on the surface of a host bacteriophage, preferably an M13 phage.

After expression and display on the surface of the bacteriophage, instead of releasing the protein of interest by incubating the bacteriophage with enterokinase, the protein of interest may be isolated by binding the expressed fusion protein with a ligand for the protein of interest, e.g., an antigen in the case of an antibody or antibody fragment of interest. The ligand may be immobilized on a column or other solid support or suspended in a liquid medium. After removal of unbound material by washing the support or filtering of the culture medium etc., the ligand/phage display complex is incubated with enterokinase to release the genetic package, and the genetic package of interest (carrying the gene encoding the displayed protein of interest) may be thereafter collected by elution from the ligand. The recovered genetic packages can then be amplified in suitable hosts. The enterokinase cleavage sequences disclosed herein may also be utilized as a cleavable linker to an inhibitor polypeptide, to control the activity, specificity, half-life or other function of a particular protein of interest. For instance, a fusion protein comprising, for example, a protease fused to one terminus of a novel enterokinase cleavage sequence, and an inhibitor for the protease fused to the other terminus of the enterokinase cleavage sequence, may be expressed from a host cell or displayed on the surface of a host cell or phage, such that the protease is inactive in the presence of the inhibitor. When activation or removal of the influence of the inhibitor is desired, incubation of the fusion protein with enterokinase dissociates the inhibitor from the protease, thereby liberating the protease of the inhibitor.

In a similar type of fusion construct, an enterokinase recognition sequence according to the invention may be used as a linking sequence between the light chain and heavy chain elements of a single chain antibody or scFv fragment that is expressed in a recombinant host cell or displayed on a display host such as a genetic package. Incubation of the fusion with enterokinase will eliminate the linkage between the heavy and light chain elements, permitting the heavy and light chain elements (e.g., $V_H$ and $V_L$ domains in the case of a scFv) to associate more freely, i.e., without any steric constraint from the linker.

The enterokinase recognition sequences disclosed herein may also be used to confirm the proper expression and/or display of a fusion protein on the surface of a host cell or bacteriophage. In this embodiment the fusion protein display comprises a protein of interest, fused to an enterokinase recognition sequence, fused to a ligand marker, for example, a streptavidin-binding peptide. After expression and display on the surface of the host cell or bacteriophage, the construct is contacted with streptavidin (Sv) immobilized on a column or other support. Hosts properly displaying the fusion will bind to immobilized ligand (e.g., Sv ) while non-displaying hosts can be washed away. Incubation with enterokinase allows isolation of the bound hosts. These display-verified hosts may then be used in selections to identify proteins of interest that bind to targets of interest, e.g., by re-culturing the recovered display-verified binders and pre-treating them with enterokinase, leaving an unencumbered protein of interest display.

The enterokinase recognition sequences of the present invention can be used in selecting proteins or peptides displayed on genetic packages. The display library is prepared with an enterokinase recognition sequence positioned between the displayed library members and the anchor domain of the display fusion protein. The library of genetic packages are brought into contact with a target protein. The target protein is immobilized either before or after it is allowed to bind members of the display library. Non-binding members of the library are washed away. The immobilized genetic packages are treated with enterokinase and packages that are released are cultured. For example, Ff packages are used to infect *E. coli*, while display yeast genetic packages are grown in suitable growth medium. The advantage of this method is that buffer conditions need not be changed and the released packages are highly likely to have been bound by way of the displayed protein or peptide rather than some non-specific interaction with the body of the genetic package.

Identification of Novel Enterokinase Recognition Sequences

To identify novel enterokinase cleavage sequences, a substrate phage library, having a diversity of about $2\times10^8$ amino acid sequences, was screened against enterokinase. The substrate phage library was designed to include a peptide-variegated region in the display polypeptide. This region consisted of 13 consecutive amino acids, and the display polypeptide design allowed any amino acid residue except cysteine to occur at each position. The substrate phage library also was characterized by inclusion of an N-terminal tandem arrangement of a linear and a disulfide-constrained streptavidin recognition sequence. The screen was carried through a total of 5 rounds of increasing stringency to obtain phage that could be released by incubation with recombinant light chain enterokinase (obtained from Novagen, Madison, Wis.) after binding to immobilized streptavidin. 90 isolates remaining after the $5^{th}$ round of screening were randomly chosen for further sequence analysis.

DNA sequence analysis of the 90 round 5 isolates demonstrated a substantial sequence collapse. When the isolates were grouped by sequence similarity, 82 of the 90 isolates contained one or more examples (for a total of 99 occurrences) of a simple dipeptide motif consisting of an acidic residue (Asp or Glu) followed on the carboxyl side by a basic residue. The observed frequencies of the dipeptides among the 99 instances were: Asp-Arg (DR) 66%, Asp-Lys (DK) 18%, Glu-Arg (ER) 14%, and Glu-Lys (EK) 4%.

Sequences that occurred multiple times were examined further in comparison to an isolate containing the known EK cleavage sequence $(Asp)_4$-Lys and an unselected (irrelevant) control. Of these isolates, several were found that cleaved more rapidly than a test sequence containing $(Asp)_4$-Lys (see Examples, infra).

Preparation of Phase Display Library

The enterokinase recognition sequences of the present invention were isolated from a diverse library of potential enterokinase recognition sequences fused to streptavidin recognition sequences displayed on the surface of bacteriophage. A phage display library with a display sequence diversity of $10^8$ or more may be constructed according to the methods disclosed, for example, in Kay et al., *Phage Display of Peptides and Proteins: A Laboratory Manual* (Academic Press, Inc., San Diego 1996) and U.S. Pat. No. 5,223,409 (Ladner et al.), and Dower et al., U.S. Pat. No. 5,432,018, incorporated herein by reference. An oligonucleotide library is inserted in an appropriate vector encoding a bacteriophage structural protein, preferably an accessible phage protein, such as a bacteriophage coat protein. Although a variety of bacteriophage may be employed in the present invention, the vector is, or is derived from, a filamentous bacteriophage, such as, for example, f1, fd, Pf1, M13, etc.

The phage vector is chosen to contain or is constructed to contain a cloning site located in the 5' region of the gene encoding the bacteriophage structural protein, so that the enterokinase recognition sequence is accessible to the enzyme in the process of identifying novel enterokinase recognition sequences.

An appropriate vector allows oriented cloning of the oligonucleotide sequences encoding the recognition sequences of the present invention so that the recognition sequence is expressed close to the N-terminus of the mature coat protein. The coat protein is typically expressed as a preprotein, having a leader sequence. Thus, it is preferred that the oligonucleotide library is inserted so that the N-terminus of the processed bacteriophage outer protein is the first residue of the peptide, i.e., between the 3'-terminus of the sequence encoding the leader protein and the 5'-terminus of the sequence encoding the mature protein or a portion of the 5'-terminus.

The library is constructed by cloning an oligonucleotide which contains the potential enterokinase recognition sequence (and a streptavidin or other ligand recognition sequence) into the selected cloning site. Using known recombinant DNA techniques (see generally, Sambrook et al., *Molecular Cloning, A Laboratory Manual*, 2d ed., Cold Spring Harbor Laboratory Press, Cold Spring Harbor, N.Y., (1989), incorporated herein by reference), an oligonucleotide may be constructed which, inter alia, removes unwanted restriction sites and adds desired ones, reconstructs the correct portions of any sequences which have been removed, inserts the spacer, conserved or framework residues, if any, and corrects the translation frame (if necessary) to produce active, infective phage. The central portion of the oligonucleotide will generally contain one or more recognition sequences and any additional residues such as, for example, any spacer or framework residues. The sequences are ultimately expressed as peptides (with or without spacer or framework residues) fused to or in the N-terminus of the mature coat protein on the outer, accessible surface of the assembled bacteriophage particles.

The variable enterokinase recognition sequences of the oligonucleotide comprise the source of the library. The size of the library will vary according to the number of variable codons, and hence the size of the peptides, which are desired. Generally the library will be at least about $10^6$ members, usually at least $10^7$ and typically $10^8$ or more members.

To generate the collection of oligonucleotides which forms a series of codons encoding a random collection of possible enterokinase recognition sequences and which is ultimately cloned into the vector, a codon motif is used, such as $(NNK)_x$, where N may be A, C, G, or T (nominally equimolar), K is G or T (nominally equimolar), and x is typically up to about 5, 6, 7, or 8 or more, thereby producing libraries of penta-, hexa-, hepta-, and octa-peptides or more. The third position may also be G or C, designated "S". Thus, NNK or NNS (i) code for all the amino acids, (ii) code for only one stop codon, and (iii) reduce the range of codon bias from 6:1 to 3:1. It should be understood that with longer peptides, the size of the library which is generated may become a constraint in the cloning process. The expression of peptides from randomly generated mixtures of oligonucleotides in appropriate recombinant vectors is discussed in Oliphant et al., *Gene* 44: 177–183 (1986), incorporated herein by reference.

An exemplified codon motif, $(NNK)_6$, produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with only three-codon amino acids.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5'-OH-protecting groups, and activated by the addition of 3' O-phosphoramidite (and phosphate protection with beta cyanoethyl groups) by the method used for the activation of mononucleosides, as generally described in McBride and Caruthers, *Tetrahedron Letters* 22: 245 (1983), which is incorporated herein by reference. Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis*, M. J. Gain, ed. p. 35–82 (1984) incorporated herein by reference. Thus, this procedure generates a population of oligonucleotides for cloning that is capable of encoding an equal distribution (or a controlled unequal distribution) of the possible peptide sequences. This approach may be especially useful in generating longer peptide sequences, since the range of bias produced by the $(NNK)_6$ motif increases by three-fold with each additional amino acid residue.

When the codon motif is $(NNK)_n$, as defined above, and when n equals 8, there are $2.6 \times 10^{10}$ possible octapeptides. A library containing most of the octapeptides may be difficult to produce. Thus, a sampling of the octapeptides may be accomplished by constructing a subset library using from about 0.1%, and up to as much as 1%, 5%, or 10% of the possible sequences, which subset of recombinant bacteriophage particles is then screened. As the library size increases, smaller percentages are acceptable. If desired, to extend the diversity of a subset library, the recovered phage subset may be subjected to mutagenesis and then subjected to subsequent rounds of screening. This mutagenesis step may be accomplished in two general ways: the variable region of the recovered phage may be mutagenized, or additional variable amino acids may be added to the regions adjoining the initial variable sequences according to methods well known in the art.

A variety of techniques can be used in the present invention to diversify a peptide library or to diversify around peptides found in early rounds of screening to have sufficient cleavability. In one approach, the positive phage (those identified in an early round of screening) are sequenced to determine the identity of the active peptides. Oligonucleotides are then synthesized based on these peptide sequences, employing a low level of all bases incorporated at each step to produce slight variations of the primary oligonucleotide sequences. This mixture of (slightly) degenerate oligonucleotides is then cloned into the affinity phage. This method produces systematic, controlled variations of the starting peptide sequences. It requires, however, that individual positive phage be sequenced before mutagenesis, and thus is useful for expanding the diversity of small numbers of recovered phage.

Another technique for diversifying around the recognition sequence of the selected phage-peptide involves the subtle misincorporation of nucleotide changes in the peptide through the use of the polymerase chain reaction (PCR) under low fidelity conditions. The protocol of Leund et al., *Technique* 1: 11–15 (1989), incorporated herein by reference, alters the ratios of nucleotides and the addition of manganese ions to produce a 2% mutation frequency.

Yet another approach for diversifying the selected phage involves the mutagenesis of a pool, or subset, of recovered phage. Phage recovered from screening are pooled and single stranded DNA is isolated. The DNA is mutagenized by treatment with, e.g., nitrous acid, formic acid, or hydrazine. These treatments produce a variety of damage in the DNA. The damaged DNA is then copied with reverse transcriptase which misincorporates bases when it encounters a site of damage. The segment containing the sequence encoding the variable peptide is then isolated by cutting with restriction nuclease(s) specific for sites flanking the variable region. This mutagenized segment is then recloned into undamaged vector DNA. The DNA is transformed into cells and a secondary library is constructed. The general mutagenesis method is described in detail in Myers et al., *Nucl. Acids Res.*, 13: 3131–3145 (1985), Myers et al., *Science*, 229: 242–246 (1985), and Myers, *Current Protocols in Molecular Biology*, Vol. 1, 8.3.1–8.3.6, Ausebel et al., eds. (J. Wiley and Sons, New York, 1989), each of which is incorporated herein by reference.

In the second general approach, that of adding additional amino acids to a peptide or peptides found to be cleavable, a variety of methods are available. In one, the sequences of peptides selected in early screening are determined individually and new oligonucleotides, incorporating the determined sequence and an adjoining degenerate sequence, are synthesized. These are then cloned to produce a secondary library.

In another approach which adds a second variable sequence region to a pool of peptide-bearing phage, a restriction site is installed next to the primary variable region. Preferably, the enzyme should cut outside of its recognition sequence, such as BspMI which cuts leaving a four base 5' overhang, four bases to the 3' side of the recognition site. Thus, the recognition site may be placed four bases from the primary degenerate region. To insert a second variable region, the pool of phage DNA is digested and blunt-ended by filling in the overhang with Klenow fragment. Double-stranded, blunt-ended, degenerately synthesized oligonucleotides are then ligated into this site to produce a second variable region juxtaposed to the primary variable region. This secondary library is then amplified and screened as before.

The peptide libraries, as described herein, have been used to identify novel amino acid sequences that may be recognized and cleaved by the enzyme enterokinase. This procedure may also be employed to identify the site-specificity of other protein modifying enzymes. By way of example, as described in Dower supra, factor $X_a$ cleaves after the sequence Ile-Glu-Gly-Arg. A library of variable region codons may be constructed, for example in M13 phage for display with pIII, having the basic structure: signal sequence—variable region—Tyr-Gly-Gly-Phe-Leu—pIII. Phage from the library are then exposed to factor $X_a$ and then screened on an antibody (e.g., 3E7), which is specific for N-terminally exposed Tyr-Gly-Gly-Phe-Leu. A pre-cleavage screening step with 3E7 can be employed to eliminate clones cleaved by *E. coli* proteases. Only members of the library with random sequences compatible with cleavage with factor $X_a$ are isolated after screening, which sequences mimic the Ile-Glu-Gly-Arg site.

Another approach to protease substrate identification involves placing the variable region between the carrier protein and a reporter sequence that is used to immobilize the complex (e.g., Tyr-Gly-Gly-Phe-Leu). Libraries are immobilized using a receptor that binds the reporter sequence (e.g., 3E7 antibody). Phage clones having sequences compatible with cleavage are released by treatment with the desired protease.

To facilitate identification of the novel enterokinase recognition sequences of the present invention, a ligand recognition sequence, such as, for example SEQ ID NO:5 may be included in the phage library as a fusion partner attached to the potential EK recognition sequence. According to this method, the streptavidin binding peptide (e.g., SEQ ID NO:5) is expressed on the surface of the coat protein along with the enterokinase cleavage sequence. The resulting constructs, which have the basic structure: phage—EK recognition sequence—streptavidin binding peptide, are then bound to streptavidin (or avidin) through the streptavidin binding peptide moiety. The streptavidin may be immobilized on a surface such as a microtiter plate or on an affinity column. Alternatively, the streptavidin may be labeled, for example with a fluorophore, to tag the active phage peptide for detection and/or isolation by sorting procedures, e.g., on a fluorescence-activated cell sorter.

Phage which express peptides without the desired specificity are removed by washing. The degree and stringency of washing required will be determined for each ligand/enterokinase recognition sequence. A certain degree of control can be exerted over the binding characteristics of the peptides to be recovered by adjusting the conditions of the binding incubation and the subsequent washing or alternatively, as disclosed herein, by modifying the recognition sequences to increase their cleavage efficiency or rate.

Once a peptide sequence that imparts some affinity and specificity for the ligand binding partner is known, the diversity around this core sequence may be varied to affect binding affinity. For instance, variable peptide regions may be placed on one or both ends of the identified sequence. The known sequence may be identified from the literature, as in the case of Arg-Gly-Asp and the integrin family of receptors, for example, as described in Ruoslahti and Pierschbacher, *Science*, 238: 491–497 (1987), or may be derived from earlier rounds of screening, as in the context of the present invention.

Since a useful enterokinase recognition sequence is already known, namely (Asp)$_4$-Lys-Xaa (SEQ ID NO:8), where Xaa is Ile in the native trypsinogen site or is any amino acid when incorporated in a synthetic EK-cleavable fusion protein, a practical standard for screening a phage display library for novel enterokinase recognition sequences was presented, in that cleavage sequences that were less specific or had a rate of cleavage only comparable to or slower than (Asp)$_4$-Lys-Xaa would be less desirable. Accordingly, although many novel enterokinase cleavage sequences may be discovered by the methods outlined above, we concentrated on isolation of enterokinase cleavage sequences providing advantages in comparison to (Asp)$_4$-Lys-Xaa (SEQ ID NO:8).

Synthesis of Peptides

Following the procedures outlined above, the synthetic polynucleotides coding for novel enterokinase recognition sequences expressed in recombinant phage recovered from the screening process may be isolated and sequenced, revealing the encoded amino acid sequences. After analysis of the recognition sequences to identify potential consensus sequences, recognition motifs, or recognition domains, it is desirable to vary these sequences to evaluate them as potential additional enterokinase recognition sequences. By chemically synthesizing peptide sequences of predetermined sequence and length, additional enterokinase recognition sequences may be evaluated and there is a strong possibility of identifying additional sequences with specificity and cleavage rates that are better than the isolates identified from the original phage library.

Synthesis may be carried out by methodologies well known to those skilled in the art (see, Kelley et al. in *Genetic Engineering Principles and Methods*, (Setlow, J. K., ed.), Plenum Press, NY., (1990) vol. 12, pp. 1–19; Stewart et al., *Solid-Phase Peptide Synthesis* (1989), W. H. Freeman Co., San Francisco) incorporated herein by reference. The enterokinase recognition sequences of the present invention can be made either by chemical synthesis or by semisynthesis. The chemical synthesis or semisynthesis methods allow the possibility of non-natural amino acid residues to be incorporated.

Enterokinase recognition peptides of the present invention are preferably prepared using solid phase peptide synthesis (Merrifield, *J. Am. Chem. Soc.*, 85: 2149 (1963); Houghten, *Proc. Natl. Acad. Sci. USA*, 82: 5132 (1985)) incorporated herein by reference. Solid phase synthesis begins at the carboxy-terminus of the putative peptide by coupling a protected amino acid to a suitable resin, which reacts with the carboxy group of the C-terminal amino acid to form a bond that is readily cleaved later, such as a halomethyl resin, e.g., chloromethyl resin and bromomethyl resin, hydroxymethyl resin, aminomethyl resin, benzhydrylamine resin, or t-alkyloxycarbonyl-hydrazide resin. After removal of the α-amino protecting group with, for example, trifluoroacetic acid (TFA) in methylene chloride and neutralizing in, for example, TEA, the next cycle in the synthesis is ready to proceed. The remaining α-amino and, if necessary, side-chain-protected amino acids are then coupled sequentially in the desired order by condensation to obtain an intermediate compound connected to the resin. Alternatively, some amino acids may be coupled to one another forming an oligopeptide prior to addition of the oligopeptide to the growing solid phase polypeptide chain.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method), and Woodward reagent K method.

Common to chemical synthesis of peptides is the protection of the reactive side-chain groups of the various amino acid moieties with suitable protecting groups at that site until the group is ultimately removed after the chain has been completely assembled. Also common is the protection of the α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The typical protective groups for protecting the α-and ε-amino side chain groups are exemplified by benzyloxycarbonyl (Z), isonicotinyloxycarbonyl (iNOC), O-chlorobenzyloxycarbonyl [Z(NO$_2$)], p-methoxybenzyloxycarbonyl [Z(OMe)], t-butoxycarbonyl (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylphosphinothioyl (Mpt), and the like.

As protective groups for the carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb), etc., and the hydroxyl group in the serine can be protected with benzyl, t-butyl, acetyl, tetrahydropyranyl, etc.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide. Upon pH adjustment, the polypeptide takes its desired conformational arrangement.

Polypeptides according to the invention may also be prepared commercially by companies providing peptide synthesis as a service (e.g., BACHEM Bioscience, Inc., King of Prussia, PA; Quality Controlled Biochemicals, Inc., Hopkinton, Mass.).

Preparation of Fusion Proteins

According to the present invention, the novel enterokinase recognition sequences may be used to isolate and purify a protein of interest or a fragment thereof. By this method, the protein of interest is present as one domain of a recombinant fusion protein also including a novel enterokinase recognition sequence according to the present invention as another domain. Preferably, the first amino acid of the protein of interest is linked C-terminal to the EK cleavage sequence, and most preferably the N-terminal amino acid of the protein of interest takes the $P_1'$ position of the enterokinase recognition sequence. In this way, cleavage by enterokinase will separate the protein of interest exactly at the initial amino acid residue, avoiding any necessity of further treatment to remove extraneous N-terminal amino acids from the protein of interest.

The novel EK recognition sequence is also preferably ligated at its amino-terminal end to a ligand recognition sequence as the third domain of a fusion protein, facilitating immobilization to a ligand binding partner, such as, for instance, streptavidin.

A fusion protein is constructed using DNA manipulations according to conventional methods of genetic engineering (see, Sambrook J., Fritsch, E. F. and Maniatis T., *Molecular Cloning; A Laboratory Manual*, Cold Spring Harbor Laboratory Press, Cold Spring Harbor, N.Y. 1989). The preferred arrangement of the domains of a fusion protein designed for the recovery of the protein of interest will be (moving from N-terminal to C-terminal): a ligand recognition sequence, an enterokinase recognition sequence and a protein of interest. In constructing the preferred fusion protein of the present invention, a polynucleotide coding for the ligand recognition sequence is joined 5' and in frame to a polynucleotide coding for an enterokinase recognition sequence, which, in turn, is linked 5' and in frame to a polynucleotide coding for the protein of interest. Preferably, the codon for the N-terminal amino acid of the protein of interest will be positioned so as to take the $P_1'$ position (i.e., just C-terminal to the scissile bond of the EK cleavage sequence) in the fusion protein construct. The fusion protein expression constuct will also typically include a promoter for directing transcription in a selected host, a ribosome binding site, and a secretion signal peptide for directing secretion of the fusion protein from a transformed host cell.

The plasmid containing the nucleotides coding for the fusion protein of the present invention may be constructed by ligating the DNA fragments into an expression vector of choice by techniques well known in the art. For the construction, conventional DNA ligation techniques may be used. For instance, using the restriction enzyme method, the nucleotide sequences which comprise the sequences that are translated into the fusion protein, after isolation and/or synthesis, may be restriction digested at strategic sites to create DNA sequence overhangs as a template for fusion to another DNA molecule having an homologous overhang or sequence. Alternatively, a single-stranded DNA overhang may be synthetically constructed onto a DNA fragment that either has an existing overhang or is blunt-ended by using techniques well known in the art. The homologous, single-stranded DNA overhangs of each nucleotide sequence are then ligated using a commercially available ligase such as, for instance, T4 DNA ligase, to create a fused DNA fragment comprising DNA from different regions of the same organism or DNA from different organisms or sources. Theoretically, the only limitation to the number of DNA fragments that may be ligated or the size of the ligated fragment is limited by the size of the fragment that can be inserted into the vector or expression vector of choice.

By a similar method, the fused DNA fragments are then ligated into an expression vector which has been treated with the appropriate restriction enzyme or enzymes to create a splice site within the vector that is compatible with the 5' and 3' ends of the DNA fragment to be inserted for expression. After ligation is complete, the recombinant vector is introduced into the appropriate host cell for expression of the protein of interest fused with the ligand recognition and enterokinase recognition sequences.

Isolation and Purification of a Protein of Interest

For expression of the fusion protein, cells transformed with the expression vector are grown in cell culture under conditions suitable for the expression of the protein of interest. After expression the cells may be lysed to release the fusion protein into the cell culture or preferably the fusion protein will include a signal sequence to facilitate secretion of the fusion protein into the culture medium without the need for disruption or lysis of the host cell. Secretion of the fusion protein into the culture medium is preferred, as the fusion protein may be isolated directly from the culture supernatant. If the cells require lysis, one or more additional purification steps will be necessary to separate the fusion protein from the cellular debris released upon lysis of the cells. This may result in reduced yields of the protein of interest or a diminution of its biological activity.

The fusion proteins of the present invention may be isolated and purified by standard methods including chromatography (e.g., ion exchange, affinity, sizing column chromatography, and high pressure liquid chromatography), centrifugation, differential solubility, or by any other standard technique for the purification of proteins.

In one aspect of the invention, large quantities of the fusion protein may be isolated and purified by passing the cell culture supernatant containing the expressed fusion protein over a column containing an immobilized ligand binding partner specific for the ligand recognition sequence included in the fusion protein construct, such as, for example, streptavidin (i.e., where the fusion protein contains a biotin or other streptavidin binding domain). After binding, the column is washed to remove any unbound fusion peptides. Following the wash step, the column is contacted with enterokinase under incubation conditions and enzyme concentrations suitable for cleavage of the enterokinase recognition sequence. The released protein is then eluted and recovered in substantially pure and biologically active form by standard methods known in the art. In most instances the recovered protein of interest will not require any further purification steps. Alternatively, enterokinase may be added to the culture medium prior to contacting the culture media with a ligand binding partner so as to isolate or immobilize the binding partner/EK cleavage sequence portion of the fusion protein and leave the protein of interest portion in solution.

The present invention may be further illustrated by reference to the following non-limiting examples.

EXAMPLES

Construction and Screening of Phage Display Library for EK Cleavage Sequences
(i) Construction of Substrate Phage Library A phage display library was designed for the display of an exogenous polyeptide at the N-terminus of M13 phage gene III protein. The exogenous polyeptide was an 86-mer fusion protein having tandem ligand recognition sequences, a variegated segment of thirteen amino acids serving as a template for potential EK recognition sequences, a factor Xa cleavage site, segments linking the foregoing domains and linking to the N-terminus of gene III protein. The sequence of the exogenous display polypeptide was as follows:

Tris-HCl, pH 7.4, 50 mM NaCl, 2 mM $CaCl_2$, 0.05% Triton X-100). After washing with EK assay buffer (500 µL×5), the bead bound phage were incubated with recombinant light chain enterokinase (Novagen, Madison, Wis.) in assay buffer at room temperature.

DNA sequence analysis of up to 40 randomly chosen phage isolates from each screening condition was performed at round 2 and all subsequent rounds to monitor the progress of substrate selection. The stringency of screening conditions was increased in rounds 4 and 5 as consensus sequence patterns were not clearly discernible after round 3.

In rounds 1 thru 3, two different enterokinase concentrations were used. The 320 nM susceptible phage populations were treated consistently at 320 nM enterokinase in all three rounds and the 1.3 µM enterokinase susceptible phage populations were treated consistently at that concentration in all three rounds.

In round 4, the 320 nM enterokinase susceptible phage from round 3 were bound to streptavidin beads then incubated for 30 minutes with 65 nM enterokinase in enterokinase assay buffer. The beads were pelleted by centrifugation for 30 sec in a microfuge and the supernatant containing the enterokinase-cleaved phage was removed. Fresh 65 nM enterokinase in assay buffer was added to the beads for an additional 1.5 hr incubation to cleave remaining phage.

For round 5, two aliquots of the 30 minute enterokinase-susceptible phage from round 4 were bound to separate batches of streptavidin beads for incubation in either 10 nM enterokinase or 30 nM enterokinase.

After removing the "cleaved" phage supernatants from the streptavidin beads in each round, the supernatants were mixed with two successive batches of fresh streptavidin beads for 30 minutes at room temperature to eliminate any free phage that retained the streptavidin binding domain. The final unbound phage supernatants were used to infect host *Escherichia coli* cells to amplify the phage populations for each subsequent round of screening.

The amplified phage populations from round 5 were tested for enterokinase cleavage by phage ELISA. Round 5 phage populations were screened against phage from the unselected substrate library as a negative control.

Individual phage samples were allowed to bind to streptavidin-coated microtiter wells and then subjected to

```
AEWHPQFSSPSASRPSEGPCHPQFPRCYIENLDEFRPGGSGGXXXXXXXXXXXXXGAQS (SEQ ID NO:9),

DGGGSTEHAEGGSADPSYIEGRIVGSA-(gene III protein N-terminus)
``` wherein any amino acid residue except cysteine was permitted at each X position. The underscored segments denote, moving from N-terminal to C-terminal, a linear streptavidin binding sequence, a constrained streptavidin binding loop, and a factor Xa cleavage site, respectively. This design gave a potential diversity of $4.2 \times 10^{16}$. Approximately $2 \times 10^8$ different display polypeptides were included in the library for screening.
(ii) Screening Library for Novel Enterokinase Cleavage Sequences The substrate phage library having a diversity of $2 \times 10^8$ display polypeptide sequences was screened for phage that could be released by enterokinase cleavage after binding to streptavidin immobilized on polystyrene magnetic beads.

Phage were screened for a total of five rounds. In each screening round, two aliquots of phage were allowed to bind streptavidin beads in separate tubes by incubation at room temperature for 30 minutes in EK assay buffer (20 mM different concentrations of enterokinase for 2 hours at room temperature. Unreleased phage were detected using an anti-phage antibody-horseradish peroxidase (HRP) conjugate and HRP activity assay. The decline in absorbance at 630 nm in streptavidin-bound phage with increasing enterokinase concentrations observed for the round 5 phage populations indicated successful selection for enterokinase substrates.
(iii) Identification of Specific Enterokinase Cleavage Sequences The DNA sequences of 82 of the 90 randomly chosen phage isolates from round 5, when grouped by sequence similarity, yielded a simple acidic amino acid-basic amino acid double codon motif that included a 66% frequency of the codon sequence for Asp-Arg, 14% for Glu-Arg, 18% for Asp-Lys, and 4% for Glu-Lys. The sequences from isolation rounds 2–4 were reviewed for the acid-base motif, and the single EK cleavage site peptide substrates are set forth in Tables 1, 2 and 3. Hexamers upstream (N-terminal) with respect to the scissile bond ($P_1$) were noted, as this peptide length was regarded as indicative of a high specificity substrate. The peptides are listed as heptamers including the $P_1$ amino acid residue. Amino acid residues in bold type are from the variegated region of the display peptide; amino acid residues depicted in regular type are constant residues from the phage protein.

TABLE 1

Amino Acid Sequences of Round 2 Isolates

| Isolate | Amino Acid Sequence | SEQ ID NO: |
|---|---|---|
| 02-A01 | Y E W Q D R T | 10 |
| 02-A03 | N S I K D R V | 11 |
| 02-A07 | A K A T E R H | 12 |
| 02-A09 | L G K V D R T | 13 |
| 02-A10 | G G M A D K F | 14 |
| 02-B05 | G H W L D K N | 15 |
| 02-B07 | N K A K D R M | 16 |
| 02-B11 | S E N F D K N | 17 |
| 02-C03 | L D W E D R A | 18 |
| 02-C04 | S T D A E R M | 19 |
| 02-C05 | H T F S D R Q | 20 |
| 02-C07 | G S G G D R L | 21 |
| 02-C09 | G F Y N D R M | 22 |
| 02-C10 | I M P Q D K S | 23 |
| 02-C11 | G G V E D R S | 24 |
| 02-D03 | W Q E S D R A | 25 |
| 02-E02 | G S G G D R H | 26 |
| 02-F06 | G H I F D R S | 27 |
| 02-E02 | G S G G E K L | 28 |
| 02-F01 | S G G E D R M | 29 |
| 02-F02 | G S G G E R T | 30 |
| 02-F05 | P D P Q E R Q | 31 |
| 02-F06 | Y I M G D R T | 32 |
| 02-F07 | Q N H S D R T | 33 |
| 02-F08 | I A H G E R A | 34 |
| 02-F12 | H E M N D R H | 35 |
| 02-G01 | T H N G E K M | 36 |
| 02-G02 | H D E A E K T | 37 |
| 02-G04 | G Y W I D R S | 38 |
| 02-G05 | G S G G E R L | 39 |
| 02-G06 | S G G S D R L | 40 |

TABLE 2

Amino Acid Sequences of Round 3 Isolates

| Isolate | Amino Acid Sequence | SEQ ID NO: |
|---|---|---|
| 03-A02 | A Q Y M D L M | 41 |
| 03-A03 | G S G G E R N | 42 |
| 03-A04 | G S G G E N G | 43 |
| 03-A06 | E N Y E E R T | 44 |
| 03-A07 | N I Y G D R I | 45 |
| 03-A12 | G G F V D K Q | 46 |
| 03-B01 | G S G G E K V | 47 |
| 03-B04 | G K F E D R N | 48 |
| 03-B08 | P A H T D R D | 49 |
| 03-B09 | Q Q M H D R F | 50 |
| 03-B12 | D M G Y D R G | 51 |
| 03-C02 | S G G D E K E | 52 |
| 03-C04 | I E S A D R T | 53 |
| 03-C11 | R N M D E R A | 54 |
| 03-D03 | T V G M D K F | 55 |
| 03-D10 | G S G G D R F | 56 |
| 03-D11 | R H N Y D R I | 57 |
| 03-D12 | V Y H V D K M | 58 |
| 03-E01 | G S G G E R N | 59 |
| 03-F01 | G G K Y D R M | 60 |
| 03-G01 | G G N D D K M | 61 |
| 03-H02 | A A V E D R N | 62 |
| 03-H05 | P C K D E R F | 63 |
| 03-H12 | G S E L D R M | 64 |

TABLE 3

Amino Acid Sequences of Round 4 Isolates

| Isolate | Amino Acid Sequence | SEQ ID NO: |
|---|---|---|
| 04-A01 | F S E E D R M | 65 |
| 04-A03 | G S G G E R F | 66 |
| 04-A04 | Y Q P T D R T | 67 |
| 04-A05 | S G G E D R M | 68 |
| 04-A06 | T E Q M D R M | 69 |
| 04-A07 | Q P F D D R D | 70 |
| 04-A08 | G S G G E R T | 71 |
| 04-A09 | E G M T D R L | 72 |
| 04-A10 | E I P E D R M | 73 |
| 04-A11 | G D D D D K I | 74 |
| 04-B02 | G S G G E R S | 75 |
| 04-B03 | H G Y E E R M | 76 |
| 04-B05 | K P M E E R M | 77 |
| 04-B06 | S G G N D R M | 78 |
| 04-B07 | G G T D D R F | 79 |
| 04-B08 | D V Y S E R M | 80 |
| 04-B12 | D V Y S E R M | 81 |
| 04-C01 | G S G G D R N | 82 |
| 04-C02 | D V T A D D R | 83 |
| 04-C04 | A E F A D R F | 84 |
| 04-C06 | N N S D E K I | 85 |
| 04-C08 | P G G D D R W | 86 |
| 04-C09 | S G G E E R V | 87 |
| 04-C10 | V W P D D R S | 88 |
| 04-C11 | H R Q T D R M | 89 |
| 04-D02 | K E A E D R A | 90 |
| 04-D03 | V G D D E R H | 91 |
| 04-D04 | N S M A D R N | 92 |
| 04-D06 | T E F E D K W | 93 |
| 04-D07 | E S G G E R D | 94 |
| 04-D08 | N N Y W D R M | 95 |
| 04-D09 | F S E E D R M | 96 |
| 04-D11 | E N H E E R M | 97 |
| 04-D12 | D Q M E D R Q | 98 |
| 04-E01 | E W K M D R M | 99 |
| 04-E02 | S Y T W D R S | 100 |
| 04-E03 | S F M L D R M | 101 |
| 04-E05 | T E V D D R H | 102 |
| 04-E06 | G D Q E D R M | 103 |
| 04-E07 | H N I D D R I | 104 |
| 04-E08 | A S W E D R T | 105 |
| 04-E09 | G G E D D R S | 106 |
| 04-E10 | D I Q D E R N | 107 |
| 04-F01 | D T H A D K S | 108 |
| 04-F02 | G S G G D R M | 109 |
| 04-F03 | G E I M D R S | 110 |
| 04-F05 | G S G G D K T | 111 |
| 04-F06 | G S G G D R A | 112 |
| 04-F07 | G D H L D R M | 113 |
| 04-F08 | G Q Q D D R Q | 114 |
| 04-F09 | A L A A D R M | 115 |
| 04-F10 | V G F D D R T | 116 |
| 04-F11 | Y A Q D E R T | 117 |
| 04-F12 | G G R E E R N | 118 |
| 04-G02 | G S G G D R M | 119 |
| 04-G04 | G S G G D R E | 120 |
| 04-G05 | I A Y Q D R M | 121 |
| 04-G08 | S G G E R A | 122 |
| 04-G09 | L E H S D R V | 123 |
| 04-G10 | F K P D D R M | 124 |
| 04-G11 | V P M A D R S | 125 |
| 04-G12 | G S G G E R A | 126 |
| 04-H02 | N D N D E R A | 127 |
| 04-H04 | G N Y T D R M | 128 |
| 04-H05 | G S G G E R V | 129 |
| 04-H06 | D E V H D R T | 130 |
| 04-H07 | Q H D G D K T | 131 |
| 04-H08 | T V R S E K G | 132 |
| 04-H10 | S G G T D R I | 133 |

The sequenced Round 5 EK recognition sequences having at least three amino acids from the variegated region N-terminal to the scissile bond are shown in Table 4. Sequences having more than one acid-base combination (and thus being suspected of encompassing a double cleavage site) or no acid-base combination are eliminated from the table. The hexamer including the acid-base combination and the amino acid C-terminal to the scissile bond are shown. The EK cleavage substrate was regarded as being defined by three to six amino acids upstream (N-terminal) of the scissile bond.

TABLE 4

Amino Acid Sequences of Round 5 Isolates

| Isolate | Amino Acid Sequence | SEQ ID NO: |
|---|---|---|
| 05-A02 | V M E D D R A | 134 |
| 05-A03 | G S G G E R M | 135 |
| 05-A05 | I E H D D R M | 136 |
| 05-A08 | F S E E D R M | 137 |
| 05-A10 | F S E E D R M | 138 |
| 05-A11 | D V Y S E R M | 139 |
| 05-A12 | D M F D D R M | 140 |
| 05-B01 | F S E E D R M | 141 |
| 05-B02 | E H L F D R M | 142 |
| 05-B03 | S W I S D R V | 143 |
| 05-B04 | N D E D D R M | 144 |
| 05-B05 | S L D D D R T | 145 |
| 05-B06 | G S G G D R D | 146 |
| 05-B08 | P H I E D R M | 147 |
| 05-B09 | S G G D D R H | 148 |
| 05-B10 | E V F A D R S | 149 |
| 05-B11 | G L A E D R T | 150 |
| 05-C01 | S G G D D R L | 151 |
| 05-C04 | S G G D D R M | 152 |
| 05-C05 | G L V S E R G | 153 |
| 05-C08 | G G F E D K M | 154 |
| 05-C09 | S L D D D R T | 155 |
| 05-C10 | D V Y S E R M | 156 |
| 05-D01 | N M D W D R S | 157 |
| 05-D02 | S L D D D R T | 158 |
| 05-D03 | G S G G D R M | 159 |
| 05-D05 | F S E E D R M | 160 |
| 05-D07 | S L D D D R T | 161 |
| 05-D09 | V D M H D R M | 162 |
| 05-D10 | S G G G D R M | 163 |
| 05-D12 | N V R M D R S | 164 |
| 05-E02 | S H R D E K V | 165 |
| 05-E03 | L M N D D R A | 166 |
| 05-E05 | F V M N D K G | 167 |
| 05-E06 | V S D D D R A | 168 |
| 05-E07 | G H V D D R M | 169 |
| 05-E08 | H A I E E R S | 170 |
| 05-E10 | D I N D D R S | 171 |
| 05-E11 | G S G G E R T | 172 |
| 05-E12 | A V I G D R S | 173 |
| 05-F01 | S G G E E R G | 174 |
| 05-F05 | V E F Y D R M | 175 |
| 05-F09 | G S G G E R I | 176 |
| 05-E11 | S L D D D R T | 177 |
| 05-G02 | S G G Q E R S | 178 |
| 05-G03 | D I N D D R S | 179 |
| 05-G04 | D H V W D R A | 180 |
| 05-G05 | G S G G D R I | 181 |
| 05-G06 | I E D E D R A | 182 |
| 05-G07 | M T F D E R G | 183 |
| 05-G08 | G D W D D K N | 184 |
| 05-G09 | I A Y Q D R M | 185 |
| 05-G11 | G S G G D R I | 186 |
| 05-G12 | G F V Q E R M | 187 |
| 05-H04 | D I N D D R S | 188 |
| 05-H05 | G W N D D R I | 189 |
| 05-H06 | G G F E D R L | 190 |
| 05-H08 | G S G G D R N | 191 |
| 05-H09 | A A V E D R N | 192 |
| 05-H10 | D Y R L D R I | 193 |
| 05-H11 | G D D D D K I | 194 |

The five sequences that occurred in the selected phage more than once are shown in Table 5, below. Interestingly, only one instance of the native enterokinase substrate sequence (Asp)$_4$-Lys-Ile was identified (05-H11).

TABLE 5

Amino acid sequences of EK recognition sequences from Substrate Phage Library Isolates that occurred more than once among 82 sequenced isolates

| phage isolate | variable region sequence | frequency | SEQ ID NO: |
|---|---|---|---|
| 5-A01 | DRMYQLDKTGFMI | 11 | 195 |
| 5-A08 | DMFSEEDRMMQMQ | 4 | 137 |
| 5-A11 | DLNDVYSERMAMW | 2 | 139 |
| 5-B05 | SLDDDRTVSPKFW | 5 | 145 |
| 5-H04 | DINDDRSLFSESS | 3 | 188 |
| 5-H11 | MGDDDDKIYVYKT | 1 | 194 |
| 5-F08 | AVLSNVMHSDDWT | unselected control | 196 |

Figure 2:
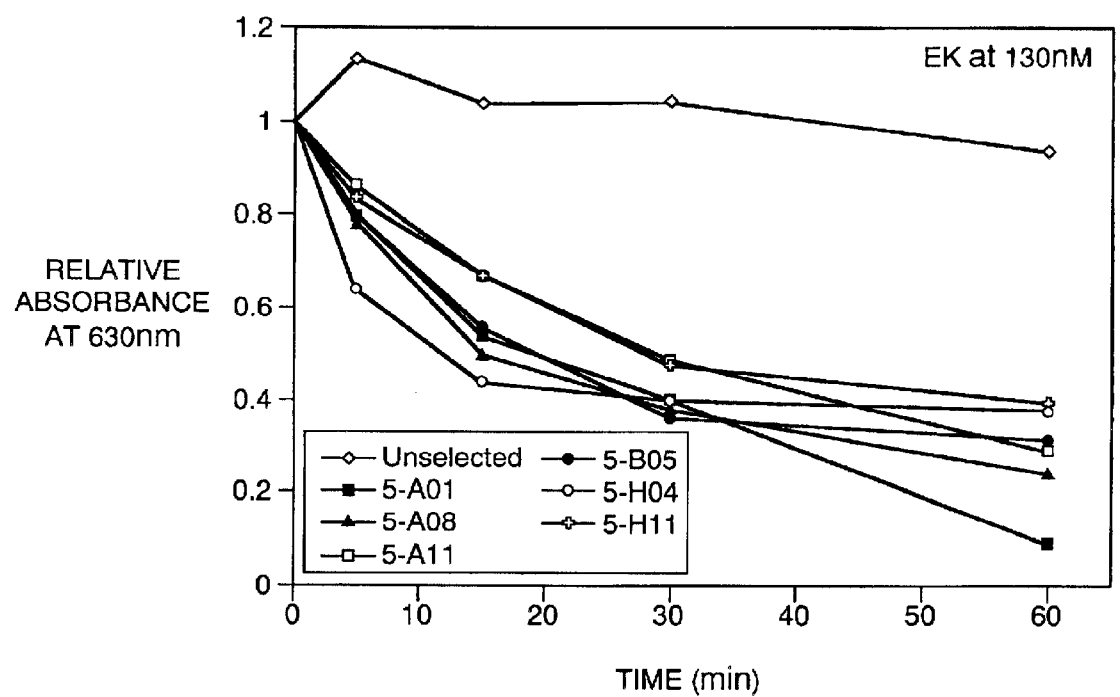

Phage displaying each of the sequences shown in Table 5 were tested individually for kinetics of enterokinase cleavage using a phage ELISA. Streptavidin-bound phage were treated with either 30 nM or 130 nM enterokinase for 30 minutes. The time courses of phage release are shown in FIG. 1 (release at 30 nM EK) and FIG. 2 (release at 130 nM EK). Phage from the unselected substrate library were used as a control, i.e., isolate 5-F08. (SEQ ID NO:196).

The kinetics of enterokinase cleavage differed between the two concentrations of enterokinase used. At 30 nM enterokinase, there was a lag in phage release which was not observed at 130 nM enterokinase. This may be attributed to a requirement for the enzyme to cut three to five copies of the substrate peptide on a single phage for successful release.

In comparing the enterokinase cleavage rates of each phage type, isolate 5-H04 (SEQ ID NO:188) shown in Table 5 was the most readily cut, and the cleavage rate for the (Asp)$_4$-Lys-containing recognition sequence 5-H11 (SEQ ID NO:194) was slower than for at least three of the other isolates, i.e., 5-A08 (SEQ ID NO:137), 5-B05 (SEQ ID NO:145) and 5-H04 (SEQ ID NO:188).

(iv) Comparative Analysis of Preferred Enterokinase Cleavage Sites

To further test the predicted cleavage site as well as the rates and extent of cleavage, seven test peptides shown in Table 6 were chemically synthesized, contacted with enterokinase, and analyzed by HPLC and mass spectrometric analysis.

TABLE 6

Synthetic Test Peptides

| test peptide sequence ↑ = predicted cleavage site | SEQ ID NO: |
|---|---|
| GDDDDK↑IYV (positive control) | 197 |
| AVLSNVMFII (negative control) | 198 |
| GNYTDR↑MFI | 199 |
| DINDDR↑SLF | 200 |
| NKAKDR↑MFI | 201 |
| GNYTDR↑RFI | 202 |
| GNYTDR↑YFI | 203 |

To test the predicted cleavage site, i.e., following the acid-base dipeptide motif, 60 to 100 μg of each test peptide was digested to completion (36–48 hrs) with 20U of recombinant light chain enterokinase (Novagen) and analyzed by reverse phase HPLC. Product peaks were eluted with a water/acetonitrile (H$_2$O/ACN) gradient and identified by electrospray mass spectroscopy. The results of the cleavage test are shown in Table 7.

TABLE 7

EK Cleavage Products

| Test Peptide | product peak | recovered product | % ACN |
|---|---|---|---|
| GDDDDK↑IYV | 1 | — | |
| | 2 | IYV | 20 |
| AVLSNVMFT | 1 | — | |
| | 2 | — | |
| GNYTDR↑MFI | 1 | GNYTDR | 9 |
| | 2 | MET | 23 |
| DINDDR↑SLF | 1 | DINDDR | 8 |
| | 2 | SLF | 21 |
| NKAKDR↑MFI | 1 | — | |
| | 2 | MFI | 23 |
| GNYTDR↑RFI | 1 | GNYTDR | 9 |
| | 2 | RFI | 17 |
| GNYTDR↑YEI | 1 | GNYTDR | 9 |
| | 2 | YFI | 22 |

HPLC demonstrated all digestions were carried to completion (except for the negative control which was not cleaved at all). "% ACN" estimates the position in the H₂O/Acetonitrile gradient at which the indicated cleavage fragment eluted. The expected product peaks for GDDDDK (residue 1–6 SEQ ID NO:197) and NKAKDR (residues 1–6, SEQ ID NO:201) were not detected by HPLC, but the cleavage site could be determined from analyzing the alternate product peak, i.e., the peptide to the C-terminal side of the cleavage site.

Results demonstrated that in all cases, enterokinase-catalyzed hydrolysis of the peptide bond occurred at the anticipated position. (See arrows in Table 6.) No cleavage occurred with the negative control peptide (SEQ ID NO:198).

(v) Relative Rate of Cleavage

Peptides were digested with enterokinase and aliquots tested at timed intervals by HPLC to quantitate the extent of cleavage. For each test peptide, about 500 μM of peptide were digested with 50 nM of recombinant light chain enterokinase. The seven synthetic peptides were compared with a commercially available standard EK cleavage substrate, GDDDDK-β-naphthylamine (GDDDDK-βNA, SEQ ID NO:203; from BACHEM, King of Prussia, Pa.), having a fluorescent leaving group that increases in fluorescence when it is cleaved. The molar rates of substrate cleavage are shown in Table 8.

TABLE 8

Relative Rates of Cleavage

| Test Peptide | Cleavage Rate (nmole/min.) | rate relative to standard substrate |
|---|---|---|
| GDDDDK-βNA | 0.46 | (1.0) |
| GDDDDKIYV | 0.34 | 0.7 |
| GNYTDRMFI | 0.81 | 1.8 |
| DINDDRSLF | 1/43 | 3.1 |
| NKAKDRMFI | 0.26* | 0.6 |
| GNYTDRRFI | 0.18 | 0.4 |
| GNYTDRYFI | 0.24 | 0.5 |

* results estimated due to peakoverlap

Peptides GNYTDRMFI (SEQ ID NO:199) and DINDDRSLF (SEQ ID NO:200) were cleaved significantly more rapidly than the two control peptides that included the native enterokinase recognition sequence, i.e., GDDDDKIYV (SEQ ID NO:197) and GDDDDK-βNA (SEQ ID NO:203). These two control peptides were cleaved at nearly equal rates and more rapidly than the remaining three peptides tested.

(vi) Substrate Competition with Reference Peptide

Rates of substrate hydrolysis depends on several factors, namely, concentration of enzyme and substrate, $K_m$ (Michaelis constant) values, and $k_{cat}$ (catalytic rate constant) values. One way to compare the relative efficiencies with which a protease hydrolyses two substrates (a and b) is to simultaneously incubate both substrates in a single reaction with the enzyme and measure the rates of product formation for each ($V_a$ and $V_b$). If the total product formation is low (<10%), the starting concentrations of the two competing substrates are the same, and the reaction is performed at steady-state:

$$V_a/V_b = (k_{cat}/K_m)_a / (k_{cat}/K_m)_b$$

Relative ratios of $k_{cat}/K_m$ can be determined from relative rates of substrate hydrolysis.

To compare the relative efficiency of hydrolysis by enterokinase, reference peptide (GDDDDK-βNA, 250 μM, SEQ ID NO:203) was incubated simultaneously with one of the test peptides (250 μM), treated with enterokinase, and the relative rate of product formation measured. The products were quantitated by HPLC and initial cleavage rates calculated. Table 9 shows the individual cleavage rates for each peptide and the relative ratio of test peptide cleavage rate to reference peptide cleavage rate.

TABLE 9

Relative Hydrolysis Rates in Competitive Assay

| Test Peptide | test peptide rate (Va) | reference peptide rate (Vb) | ratio (Va/Vb) |
|---|---|---|---|
| GDDDDKIYV | 0.028 | 0.027 | 1.0 |
| DINDDRSLF | 0.18 | 0.006 | 30 |
| GNYTDRMFI | 0.038 | 0.011 | 3.5 |

The results demonstrated that the peptide Asp-Ile-Asn-Asp-Asp-Arg-Xaa (SEQ ID NO:204) serves as an excellent substrate for cleavage by enterokinase, where the scissile bond is between Arg and Xaa, and where Xaa can be any amino acid, e.g., the first amino acid residue of a polypeptide to be cleaved from the substrate. The cleavage rate of the test peptide including SEQ ID NO:204 was 3.1 times the rate of the reference peptide when tested individually at 500 μM. The ratio $k_{cat}/K_m$ was 30 times greater than that of the reference peptide when tested in competition at 250 μM. The results further point to the substrate peptide Gly-Asn-Tyr-Thr-Asp-Arg-Xaa (SEQ ID NO:205) as superior to the known substrate (Asp)₄-Lys. The test peptide including SEQ ID NO:205 was 1.8 times the rate of the reference peptide when tested individually at 500 μM, and the ratio $k_{cat}/K_m$ was 3.5 times greater than that of the reference peptide when tested in competition at 250 μM.

(vii) Identity of Residues on C-terminal Side of Scissile Bond

Additional experiments were performed to test whether the discovered EK recognition substrates would show a preference for the identity of the amino acid in the $P_1'$ position, that is, at the position that would be the N-terminus of a polypeptide cleaved from the EK recognition substrate. The round 5 isolates were selected for the most efficient cleavage by enterokinase. While it is useful to determine which amino acids at the $P_1'$ position promote the most efficient cleavage by enterokinase, it is also important to know all the amino acids at the $P_1'$ position that promote any cleavage by enterokinase.

DNA sequencing of the phage isolates identified phage clones having 16 of the 20 amino acids at the $P_1'$ position following the Asp-Arg (DR) motif. Only four amino acids were not observed in any of the isolates at the $P_1'$ position following Asp-Arg, among those isolates sequenced: Lys, Pro, Arg and Cys (which was not permitted in the 13-mer variable portion when the substrate phage library was generated). The absence of any phage isolates exhibiting these amino acids at the $P_1'$ position does not mean that an EK recognition sequence such as Asp-Ile-Asn-Asp-Asp-Arg-Xaa (SEQ ID NO:204) having Lys, Pro, Arg or Cys at the Xaa position will not be cleaved; rather it indicates that such recognition sequences will be cleaved less efficiently than recognition sequences having the other amino acids at the Xaa ($P_1'$) position.

A phage ELISA assay was used to test examples of $P_1'$ residues for EK cleavage. 17 isolates from rounds 2–5 of screening and exhibiting the Asp-Arg motif before the scissile bond ($P_2$-$P_1$) were chosen for enterokinase cleavage analysis. Phage were bound to streptavidin immobilized in microtiter wells and then treated with either 100 nM or 300 nM recombinant light chain enterokinase for 30 minutes. For each isolate, ELISA signals obtained after entrokinase treatments were compared to the signal obtained in the absence of enterokinase treatment. Three negative controls were included: the unselected substrate phage library, isolate 5-F08 (SEQ ID NO:196) containing no cleavage sites, and a phage with an irrelevant but functional display peptide, having a thrombin cleavage site in place of the varied (13-mer) sequence.

The results showed that at the 100 nM concentration, phage displaying Met, Thr, Ser, or Ala residues at the $P_1'$ position were most sensitive to enterokinase treatment, phage displaying residues Asp, Leu, Phe, Asn, Trp, Ile, Gln, or Glu residues at the $P_1'$ position were less sensitive to 100 nM enterokinase treatment, and phage displaying residues His, Val, Gly, and Tyr at the $P_1'$ position were most resistant to enterokinase treatment. All of the phage isolates were readily cleaved when the enterokinase concentration was raised to 300 nM.

Analysis of the sequence information from screening Rounds 4 and 5 was performed to detect preferences for amino acids at the positions upstream of the scissile bond, in order to select preferred EK cleavage sequences. For the most numerous group, i.e., cleavage sequences having the Asp-Arg motif at the $P_2$ and $P_1$ positions, an amino acid was regarded as preferred at a given position in the sequence if it occurred in five or more isolates. Where a phage residue occurred at a given position, it was not counted. From this analysis, a family of preferred EK recognitions sequences was defined having the following formula:

$Xaa_1$-$Xaa_2$-$Xaa_3$-$Xaa_4$-Asp-Arg-$Xaa_5$ (SEQ ID NO:206), wherein $Xaa_1$ is an optional amino acid residue which, if present, is Ala, Asp, Glu, Phe, Gly, Ile, Asn, Ser, or Val; $Xaa_2$ is an optional amino acid residue which, if present, is Ala, Asp, Glu, His, Ile, Leu, Met, Gln, or Ser; $Xaa_3$ is an optional amino acid residue which, if present, is Asp, Glu, Phe, His, Ile, Met, Asn, Pro, Val, or Trp; $Xaa_4$ is Ala, Asp, Glu, or Thr; and $Xaa_5$ can be any amino acid residue.

For the next most numerous group, i.e., cleavage sequences having the Glu-Arg motif at the $P_2$ and $P_1$ positions, an amino acid was regarded as preferred at a given position in the sequence if it occurred in four or more isolates. From this analysis, a family of preferred EK recognition sequences was defined having the following formula:

$Xaa_1$-$Xaa_2$-$Xaa_3$-$Xaa_4$-Glu-Arg-$Xaa_5$ (SEQ ID NO:207), wherein $Xaa_1$ is an optional amino acid residue which, if present, is Asp or Glu; $Xaa_2$ is an optional amino acid residue which, if present, is Val; $Xaa_3$ is an optional amino acid residue which, if present, is Tyr; $Xaa_4$ is Asp, Glu, or Ser; and $Xaa_5$ can be any amino acid residue.

Analysis of the sequences from Rounds 2–4 having the other acid-base combinations, i.e. Asp-Lys and Glu-Lys at the $P_2$ and $P_1$ positions, did not reveal any preferences at any of the upstream positions $P_3$, $P_4$, $P_5$ or $P_6$.

Following the foregoing description, additional enterokinase cleavage sequences can be identified and synthesized, and utilized in fusion protein expression to simplify purification of any protein of interest. By following the procedures described herein, several novel cleavage sequences were discovered, and surprisingly two were tested that showed rates of cleavage several times that of the native EK recognition sequence of $(Asp)_4$-Lys-Ile (SEQ ID NO:8). Additional EK recognition sequences will become apparent to those skilled in the art following the teachings herein. For example, minor modifications to the EK cleavable recognition sequences disclosed herein may be made to improve ease of synthesis or some other property without eliminating EK recognition and without departing from the scope of this discovery.

Likewise, truncation of the preferred EK recognition sequences by substitution at positions distal from the scissile bond (e.g., sequences corresponding to amino acids 2–6 or 3–6 or 4–6 of SEQ ID NO:1) are expected to function as EK recognition sequences, although the specificity and rate of EK cleavage of a fusion protein including them may be vastly inferior to the preferred sequences disclosed above.

It will be understood by those skilled in the art that additional substitutions, modifications and variations of the described embodiments and features may be made without departing from the invention as described above or as defined by the appended claims.

The publications cited herein are hereby incorporated by reference in their entireties.

What is claimed is:

1. A non-naturally occurring enterokinase-cleavable fusion protein comprising a polypeptide comprising the formula:

$$Z_1\text{-Xaa}_1\text{-Xaa}_2\text{-Xaa}_3\text{-Xaa}_4\text{-Asp-Arg-Xaa}_5\text{-}Z_2(\text{SEQ ID NO:1}), \quad (1)$$

wherein (a) $Z_1$ is a ligand recognition sequence;

(b) $\text{Xaa}_1\text{-Xaa}_2\text{-Xaa}_3\text{-Xaa}_4\text{-Asp-Arg}$ is an enterokinase recognition sequence, in which $\text{Xaa}_1$ is Ala, Asp, Glu, Phe, Gly, Ile, Asn, Ser, or Val;

$\text{Xaa}_2$ is Ala, Asp, Glu, His, Ile, Leu, Met, Gln or Ser;

$\text{Xaa}_3$ is Asp, Glu, Phe, His, Ile, Met, Asn, Pro, Val, or Tp; and $\text{Xaa}_4$ is Ala, Asp, Glu, or Thr; and (c) $\text{Xaa}_5\text{-}Z_2$ is a protein of interest, in which $\text{Xaa}_5$ can be any amino acid and $Z_2$ is a polypeptide of at least one amino acid.

2. The fusion protein of claim 1, wherein $\text{Xaa}_1$ is Asp, $\text{Xaa}_2$- is Ile, $\text{Xaa}_3$ is Asn, $\text{Xaa}_4$- is Asp, and $\text{Xaa}_5$- is Met, Thr, Ser, Ala, Asp, Leu, Phe, Asn, Trp, Ile, Gln, Glu, His, Val, Gly or Tyr.

3. The fusion protein of claim 1, wherein the ligand recognition sequence $Z_1$ is a streptavidin binding domain.

4. The fusion protein of claim 3, wherein the streptavidin binding domain is selected from the sequences: His-Pro-Gln-Phe (SEQ ID NO:6), Cys-His-Pro-Gln-Phe-CYS (SEQ ID NO:5), Cys-His-Pro-Gln-Phe-Cys-Ser-Trp-Arg (SEQ ID NO:7), Trp-His-Pro-Gln-Phe-Ser-Ser (SEQ ID NO:210), Pro-Cys-His-Pro-Gln-Phe-Pro-Arg-Cys-Tyr (SEQ ID NO:211), and tandemly arranged combinations and repeats thereof.

5. The fusion protein according to claim 1, wherein said ligand recognition sequence $Z_1$ comprises the Myc-tag, the Flag peptide, the KT3 epitope peptide, an α-tubulin epitope peptide, a chitin binding domain, maltose binding protein (MBP), or a T7 gene 10-protein peptide tag.

6. The fusion protein according to claim 1, wherein incubation of said polypeptide (SEQ ID NO:1) with enterokinase yields the protein of interest $\text{Xaa}_5\text{-}Z_2$.

7. The fusion protein of claim 1 wherein said ligand recognition sequence $Z_1$ comprises streptavidin or avidin.

8. The fusion protein of claim 1 wherein said ligand recognition sequence $Z_1$ comprises an antibody.

9. The fusion protein of claim 1 wherein said ligand recognition sequence $Z_1$ comprises a peptide antigen recognized by an antibody.

10. The fusion protein of claim 1 wherein said ligand recognition sequence $Z_1$ comprises a polyhistidine tag.

11. The fusion protein of claim 1 further comprising a signal sequence.

12. The fusion protein of claim 1 wherein $\text{Xaa}_1$ is Asp.

13. The fusion protein of claim 1 wherein $\text{Xaa}_2$ is Ile.

14. The fusion protein of claim 1 wherein $\text{Xaa}_3$ is Asn.

15. The fusion protein of claim 1 wherein $\text{Xaa}_4$- is Asp.

16. The fusion protein of claim 1 wherein $\text{Xaa}_5$ is Arg, Lys, Cys, Met, Thr, Ser, Ala, Asp, Leu, Phe, Asn, Trp, Ile, Gln, Glu, His, Val, Gly or Tyr.

17. The fusion protein of claim 1 wherein $\text{Xaa}_5$ is Arg, Lys, Met, Thr, Ser, Ala, Asp, Leu, Phe, Asn, Trp, Ile, Gln, Glu, His, Val, Gly or Tyr.

18. The fusion protein of claim 1 wherein $\text{Xaa}_5$ is Arg, Met, Thr, Ser, Ala, Asp, Leu, Phe, Asn, Trp, Ile, Gln, Glu, His, Val, Gly or Tyr.

19. The fusion protein of claim 1 wherein $\text{Xaa}_5$ is Met, Thr, Ser, Ala, Asp, Leu, Phe, Asn, Trp, Ile, Gln, Glu, His, Val, Gly or Tyr.

20. The fusion protein of claim 1, wherein $\text{Xaa}_1$ is Asp, $\text{Xaa}_2$ is Ile, $\text{Xaa}_3$ is Asn, and $\text{Xaa}_4$- is Asp.

21. The fusion protein of claim 1, wherein $\text{Xaa}_1$ is Ser, $\text{Xaa}_2$ is Leu, $\text{Xaa}_3$ is Asp, and $\text{Xaa}_4$- is Asp.

22. The fusion protein of claim 1, wherein $\text{Xaa}_1$ is Phe, $\text{Xaa}_2$ is Ser, $\text{Xaa}_3$ is Glu, and $\text{Xaa}_4$- is Glu.

23. The fusion protein of claim 1, wherein $\text{Xaa}_1$ is Ile, $\text{Xaa}_2$ is Glu, $\text{Xaa}_3$ is Asp, and $\text{Xaa}_4$- is Glu.

24. The fusion protein of claim 1, wherein $\text{Xaa}_1$ is Ala, $\text{Xaa}_2$ is Ala, $\text{Xaa}_3$ is Val, and $\text{Xaa}_4$- is Glu.

25. The fusion protein of claim 1 that is isolated.

26. The fusion protein of claim 2, 3, 4, 5, 6, 7, 8, 9, 10, or 11 that is isolated.

27. The fusion protein of claim 12, 13, 14, 15, 16, 17, 18, 19, 20, 21, 22, 23, or 24 that is isolated.

* * * * *